United States Patent [19]
Taicher et al.

[11] Patent Number: 6,118,272
[45] Date of Patent: *Sep. 12, 2000

[54] NUCLEAR MAGNETIC RESONANCE APPARATUS AND METHOD

[75] Inventors: Gersh Zvi Taicher; Arcady Reiderman, both of Houston, Tex.

[73] Assignee: Western Atlas International, Inc., Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/902,682

[22] Filed: Jul. 30, 1997

Related U.S. Application Data

[62] Division of application No. 08/606,089, Feb. 23, 1996, Pat. No. 5,712,566.

[51] Int. Cl.⁷ ..................................................... G01V 3/00
[52] U.S. Cl. ............................................. 324/303; 324/318
[58] Field of Search ..................................... 324/303, 300, 324/318, 322, 319, 320; 335/229

[56] References Cited

U.S. PATENT DOCUMENTS

| | | | |
|---|---|---|---|
| 4,717,876 | 1/1988 | Masi et al. ............................... | 324/303 |
| 5,471,140 | 11/1995 | Hanley ..................................... | 324/303 |
| 5,488,342 | 1/1996 | Hanley ..................................... | 324/303 |

*Primary Examiner*—Louis Arana
*Attorney, Agent, or Firm*—Richard A. Fagin

[57] ABSTRACT

A nuclear magnetic resonance apparatus including a magnet generating a static magnetic field in a first region containing materials to be analyzed. The magnet generates zero static magnetic field in a second region. The magnet has generally homogeneous magnetization along a longitudinal axis and is magnetized substantially perpendicular to the axis. The apparatus includes means for generating a radio frequency magnetic field in the first region for exciting nuclei of the materials. The means for generating the radio frequency magnetic field includes an antenna disposed within the second region. The apparatus includes means for receiving a nuclear magnetic resonance signal from the excited nuclei. In a preferred embodiment, the means for generating and means for receiving include an antenna at least partially disposed within the second region. In a specific embodiment, the antenna consists of wire coils wound in planes perpendicular to the longitudinal axis of the instrument. A high permeability ferrite is disposed inside the wire coils of the antenna.

12 Claims, 16 Drawing Sheets

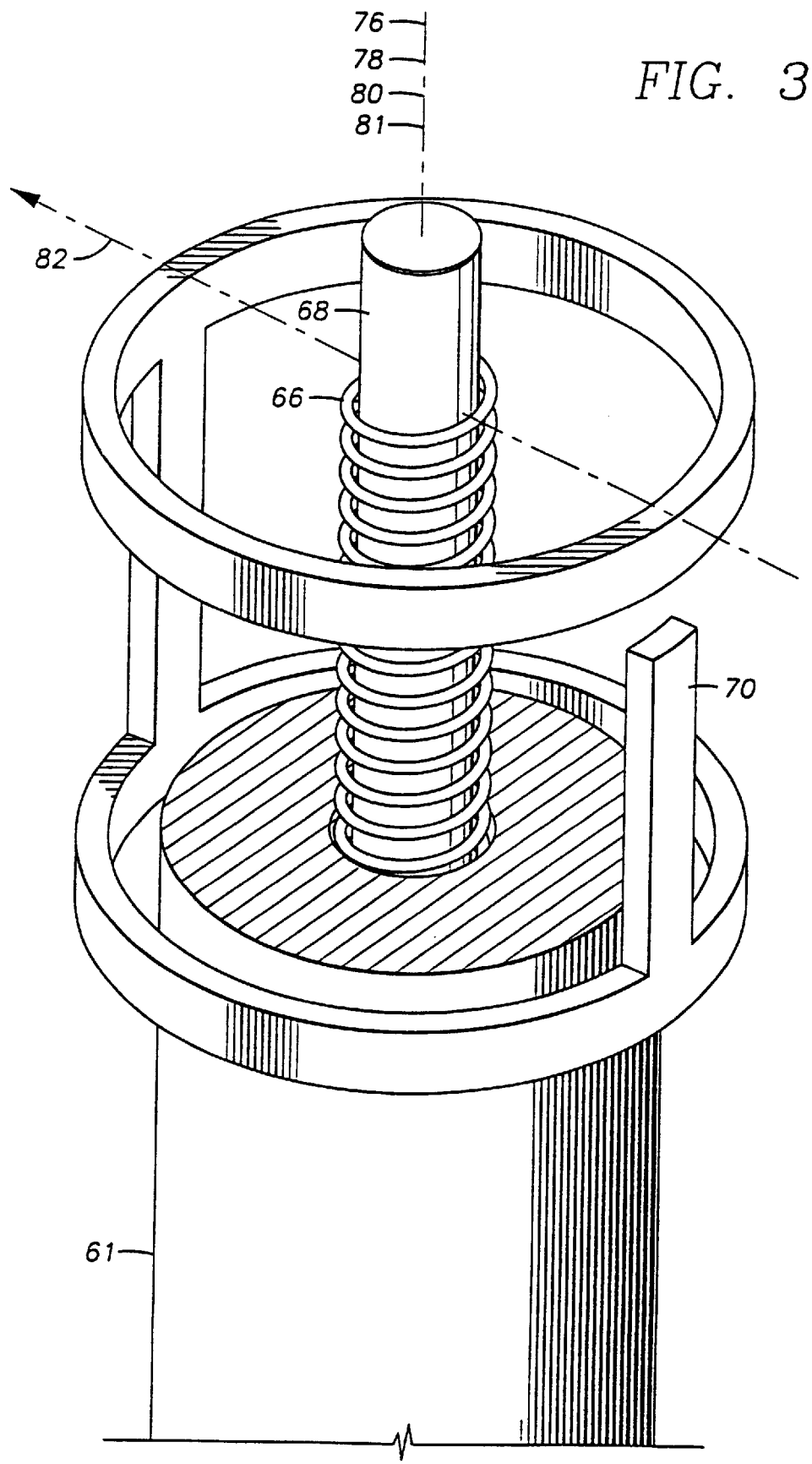

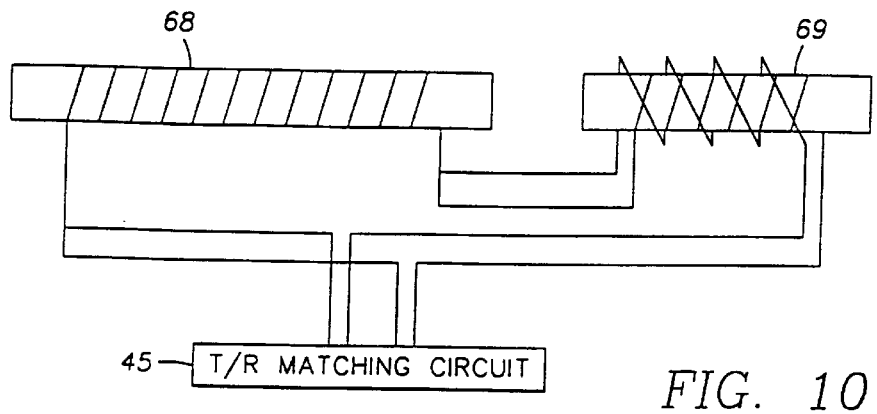
FIG. 10
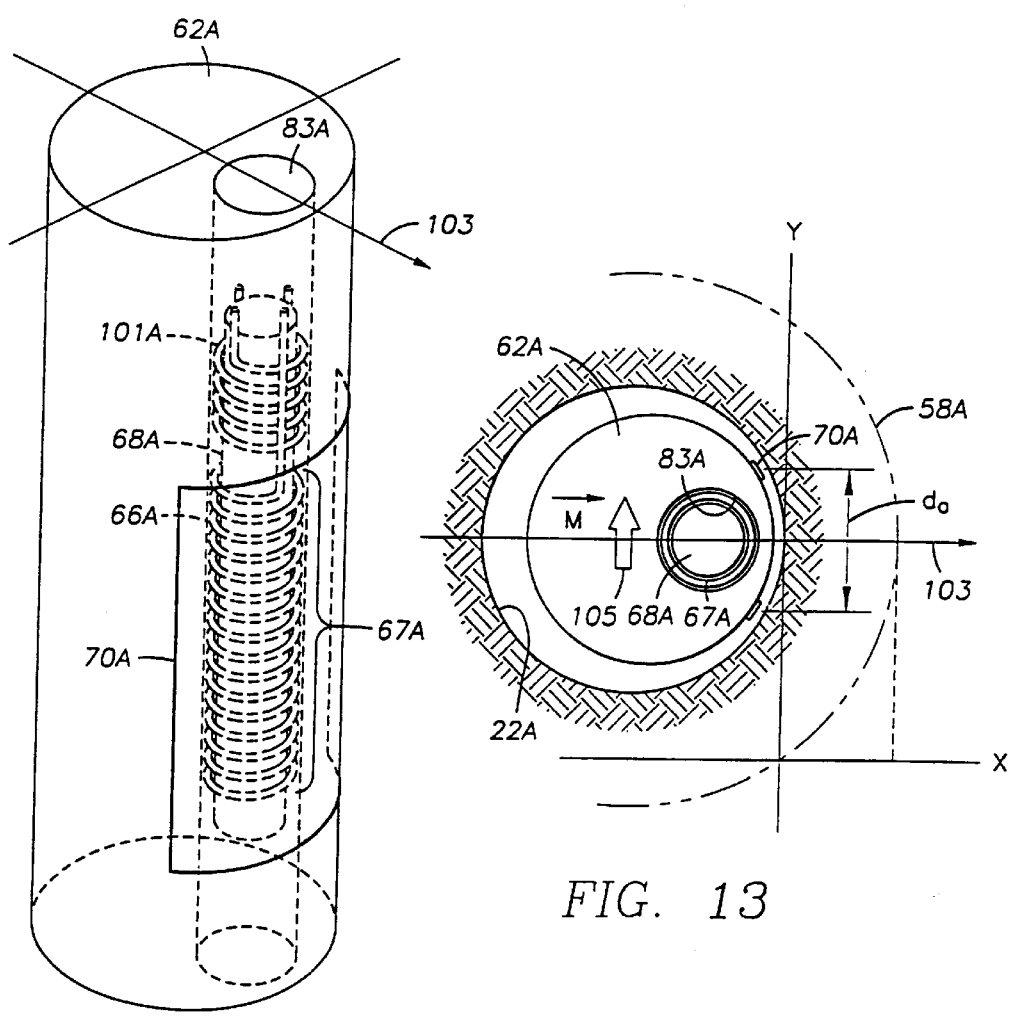
FIG. 12
FIG. 13

NUCLEAR MAGNETIC RESONANCE APPARATUS AND METHOD

CROSS REFERENCE TO RELATED APPLICATIONS

This is a division of application Ser. No. 08/606,089 filed on Feb. 23, 1996, now U.S. Pat. No. 5,712,566.

BACKGROUND OF THE INVENTION

1. Field of the Invention

The present invention is related to the field of Nuclear Magnetic Resonance (NMR) sensing apparatus and methods. More specifically, the present invention is related to NMR well logging apparatus and methods for NMR sensing within earth formations surrounding a wellbore. The present invention also relates to methods for using NMR measurements to determine properties of the earth formations surrounding the wellbore.

2. Description of the Related Art

The description of the present invention and the background thereof are approached in the context of well logging because well logging is a known application of NMR measurement techniques. It is to be explicitly understood that the present invention is not limited to the field of well logging.

NMR well logging instruments can be used for determining properties of earth formations including the fractional volume of pore space and the fractional volume of mobile fluid filling the pore spaces of the earth formations. Methods of using NMR measurements for determining the fractional volume of pore space and the fractional volume of mobile fluid are described, for example, in *Spin Echo Magnetic Resonance Logging: Porosity and Free Fluid Index Determination*, M. N. Miller et al, Society of Petroleum Engineers paper no. 20561, Richardson, Tex., 1990.

NMR oil well logging instruments known in the art typically make measurements corresponding to an amount of time for hydrogen nuclei present in the earth formations to substantially realign their spin axes, and consequently their bulk magnetization, with an applied magnetic field. The applied magnetic field is typically provided by a permanent magnet disposed in the NMR well logging instrument. The spin axes of hydrogen nuclei in the earth formation, in the aggregate, align with the magnetic field applied by the magnet.

The NMR instrument also typically includes an antenna, positioned near the magnet and shaped so that a pulse of radio frequency (RF) power conducted through the antenna induces an RF magnetic field in the earth formation. The RF magnetic field is generally orthogonal to the field applied by the magnet. This RF pulse, typically called a 90 degree pulse, has a duration and amplitude predetermined so that the spin axes of the hydrogen nuclei generally align themselves perpendicularly both to the orthogonal magnetic field induced by the RF pulse and to the magnetic field applied by the magnet. After the 90 degree pulse ends, the nuclear magnetic moments of the hydrogen nuclei gradually "relax" or return to their original alignment with the magnet's field. The amount of time taken for this relaxation, referred to as T1, is related to petrophysical properties of interest of the earth formation.

After the 90 degree pulse ends, the antenna is typically electrically connected to a receiver, which detects and measures voltages induced in the antenna by precessional rotation of the spin axes of the hydrogen nuclei. The precessional rotation generates RF energy at a frequency proportional to the strength of the magnetic field applied by the magnet, this frequency being referred to as the Larmor frequency. The constant of proportionality for the Larmor frequency is known as the gyromagnetic ratio ($y_o$). The gyromagnetic ratio is unique for each different chemical elemental isotope. The spin axes of the hydrogen nuclei gradually "dephase" because of inhomogeneities in the magnet's field and because of differences in the chemical and magnetic environment within the earth formation. Dephasing results in a rapid decrease in the magnitude of the voltages induced in the antenna. The rapid decrease in the induced voltage is referred to as the free induction decay (FID). The rate of FID is typically referred to by the notation $T2^*$. The FID decay rate consists of a first component, referred to as "true T2", which is due to internal molecular environmental effects, and a second component resulting from microscopic differences in magnetic field gradients and inhomogeneities in the earth formation. The effects of the second component can be substantially removed by a process referred to as spin-echo measurement.

Spin echo measurement can be described as in the following discussion. After a predetermined time period following the FID, another RF pulse is applied to the antenna. This RF pulse has an amplitude and duration predetermined to realign the spin axes of the hydrogen nuclei in the earth formation by an axial rotation of 180 degrees from their immediately previous orientations, and is therefore referred to as a 180 degree pulse. After the end of the 180 degree pulse, hydrogen nuclear axes that were precessing at a slower rate are then positioned so that they are "ahead" of the faster precessing spin axes. The 180 degree reorientation of the nuclear spin axes therefore causes the faster precessing axes to be reoriented "behind" the slower precessing axes. The faster precessing axes then eventually "catch up" to, and come into approximate alignment with, the slower precessing axes after the 180 degree reorientation. As a large number of the spin axes thus become "rephased" with each other, the hydrogen nuclear axial precessions are again are able to induce measurable voltages in the antenna. The voltages induced as a result of the rephasing of the hydrogen nuclear axes with each other after a 180 degree pulse are referred to as a "spin echo".

The spin echo induced voltage is typically smaller than the original voltage generated after cessation of the first RF pulse, because the aggregate nuclear axial alignment, and consequently the bulk magnetization, of the hydrogen nuclei at the time of the spin echo is at least partially realigned with the magnet's field and away from the sensitive axis of the antenna. The spin echo voltage itself decays by FID as the faster precessing nuclear axes quickly "dephase" from the slower precessing nuclear axes.

After another period of time, typically equal to two of the predetermined time periods between the initial 90 degree RF pulse and the 180 degree pulse, another RF pulse of substantially the same amplitude and duration as the 180 degree pulse is applied to the antenna. This subsequent RF pulse causes another 180 degree rotation of the spin axis orientation. This next 180 degree pulse, and the consequent spin axis realignment again causes the slower precessing spin axes to be positioned ahead of the faster precessing spin axes. Eventually another spin echo will occur and induce measurable voltages in the antenna. The induced voltages of this next spin echo will typically be smaller in amplitude than those of the previous spin echo.

Successive 180 degree RF pulses are applied to the antenna to generate successive spin echoes, each one typically having a smaller amplitude than the previous spin echo. The rate at which the peak amplitude of the spin echoes decays is related to petrophysical properties of interest of the earth formations. The number of spin echoes needed to determine the rate of spin echo amplitude decay is related to the properties of the earth formation; in some cases as many as 1,000 spin echoes may be needed to determine the amplitude decay corresponding to the properties of the earth formation which are of interest. The rate at which the peak amplitude of the spin echo measurements decays is directly related to the true T2. True T2 is related to parameters of interest in the earth formation.

One type of NMR well logging apparatus is described, for example in U.S. Pat. No. 4,350,955 issued to Jackson et al. The apparatus disclosed in the Jackson et al '955 patent includes permanent magnets configured to induce a magnetic field in the earth formations which has a toroidal volume of substantially uniform magnetic field strength. A particular drawback to the apparatus disclosed in the Jackson et al '955 patent is that the thickness of the toroidal volume is very small relative to typical rates of axial motion of well logging tools. Well logging tools, in order to be commercially useful, typically must be able to be moved axially through the wellbore at rates not less than ten feet per minute. The length of time needed to make a typical NMR spin-echo measurement set can be as long as several seconds. The NMR logging tool is therefore likely to move a substantial distance during a measurement cycle. Measurements made by the apparatus disclosed in the Jackson et al '955 patent are therefore subject to error as the apparatus is moved during logging operations, because the antenna would no longer be positioned so as to be sensitive to the same toroidal volume which was magnetized at the beginning of any measurement cycle.

Another drawback to the apparatus disclosed in the Jackson et al '955 patent is that it does not eliminate NMR signal originating within the fluid filling the wellbore.

A still further drawback to the apparatus disclosed in the Jackson et al '955 patent is that the toroidally shaped static magnetic field is subject to changes in field strength as the instrument is subjected to changes in ambient temperature and variances in the earth's magnetic field. The antenna in the Jackson et al '955 apparatus is tuned to a single frequency. If the field strength of the static magnetic field in the toroidal volume changes, the antenna may no longer be sensitive to NMR signals originating from within the toroidal volume. Using the apparatus in Jackson et al '955, it is impractical to compensate the frequency of the RF magnetic field for changes in the static magnetic field strength within the toroidal volume.

An apparatus disclosed in U.K. patent application no, 2,141,236 filed by Clow et al and published on Dec. 12, 1984 provides improved signal-to-noise ratio when compared with the apparatus of Jackson et al '955 by including a high magnetic permeability ferrite in the antenna. However, the apparatus disclosed by Clow et al is subject to similar limitations and drawbacks as is the Jackson et al '955 apparatus.

Another NMR well logging apparatus is described, for example in U.S. Pat. No. 4,710,713 issued to Taicher et al. The apparatus disclosed in the Taicher et al '713 patent includes a substantially cylindrical permanent magnet assembly which induces a static magnetic field having substantially uniform field strength within an annular cylindrical volume.

The apparatus disclosed in the Taicher et al '713 patent is subject to several drawbacks. First, because the antenna is located within the strongest part of the magnet's field, when RF electrical pulses are applied to the antenna acoustic waves can be generated in the antenna by an effect known as the "Lorenz force". The antenna returns to its original shape in a series of damped mechanical oscillations in a process referred to as "magnetoacoustic ringing". Ringing can induce large voltages in the antenna which interfere with the measurement of the voltages induced by the NMR spin echoes. Additionally, the magnet is located in the highest strength portion of the RF magnetic field. The magnet can be deformed by magnetostriction. When each RF power pulse ends, the magnet tends to return to its original shape in a series of damped mechanical oscillations, in a process referred to as "magnetostrictive ringing", which as magnetoacoustic ringing, can induce large voltages in the antenna making it difficult to measure the spin echoes.

A further drawback to the apparatus in the Taicher et al '713 patent is that the antenna induces an RF magnetic field in the formations surrounding the tool which decreases in strength as the square of the radial distance from the axis of the magnet. Moreover, a significant portion of the RF energy can be lost in an electrically conductive fluid in the wellbore. Because the signal-to-noise ratio of NMR measurements made in a gradient magnetic field is typically related to the strength of the RF magnetic field, the apparatus disclosed in the Taicher et al '713 can have difficulty obtaining measurements having sufficient signal-to-noise ratio at radial distances which are likely to be outside a zone within the earth formations known as the "invaded" zone. The invaded zone is typically formed by introduction, under differential pressure, of the liquid phase of a fluid called "drilling mud" which is used in the process of drilling the wellbore. The liquid phase displaces native fluids within the pore spaces of the earth formations proximal to the wellbore, making near-wellbore measurements unrepresentative of the native fluid content of the earth formations.

Still another drawback to the apparatus disclosed in Taicher et al '713 is that the antenna length is related to the vertical resolution required by the system designer. Typically, the vertical resolution is preferred to be very short. If the antenna in Taicher et al '713 is not made substantially longer than the diameter of the sensitive volume within the earth formation, the strength of the RF magnetic field can decrease faster than the square of the radial distance from the axis of the antenna. Lines of equal RF magnetic field strength can then become substantially elliptically shaped, which does not match the lines of equal strength of the static magnetic field. This drawback can significantly limit the ability of the apparatus in Taicher et al '713 to make measurements outside the invaded zone.

Another drawback to the apparatus of the Taicher et al '713 patent is that the antenna must be connected to complicated, difficult to build tuning circuitry in order to establish an operating frequency for the RF pulses and to receive the spin-echo emitted energy at that same frequency. It can be desirable to operate the antenna at a plurality of substantially different frequencies in order to measure properties of the earth formation at a plurality of radial distances from the axis of the NMR logging tool. Operating the antenna of the apparatus in the Taicher et al '713 patent at substantially different frequencies can be difficult and expensive, as the antenna cannot be retuned to a different frequency during operation except by connection to different transmitter and receiver circuits each having different tuned electrical characteristics.

Another NMR logging apparatus, known as the Combinable Magnetic Resonance (CMR) logging tool, is described in U.S. Pat. No. 5,055,787 issued to Kleinberg et al. The CMR logging tool includes permanent magnets arranged to induce a magnetic field in the earth formation having substantially zero field gradient within a predetermined sensitive volume. The magnets are arranged in a portion of the tool housing which is typically placed in contact with the wall of the wellbore. The antenna in the CMR tool is positioned in a recess located external to the tool housing, enabling the tool housing to be constructed of high strength material such as steel. A drawback to the CMR tool is that its sensitive volume is only about 0.8 cm away from the tool surface and extends only to about 2.5 cm radially outward from the tool surface. Measurements made by the CMR tool are therefore subject to large error caused by, among other things, roughness in the wall of the wellbore, by deposits of the solid phase of the drilling mud (called "mudcake") onto the wall of the wellbore in any substantial thickness, and by the fluid content of the formation in the invaded zone.

All of the prior art NMR well logging instruments described herein typically have antennas for generating the RF magnetic field and for receiving the NMR signals which are substantially the same length as the axial extent of the static magnetic field. A drawback to prior art NMR apparatus having such antenna dimensions is that measurements made which the instrument is moving are subject to significant error. The first source of error is that the RF magnetic field may be generated in a region different from that which is completely "prepolarized" by the static magnetic field. A second source of error is that the receiving antenna may be sensitive to an axial region which is different from the axial region in which the NMR signal is likely to originate, as the instrument is axially moved during measurement.

Accordingly, it is an object of the present invention to provide an NMR well logging apparatus which provides more accurate measurements while the apparatus is moved axially through the wellbore.

It is another object of the present invention to provide an NMR well logging apparatus which has substantially reduced effects of magnetoacoustic and magnetostrictive ringing.

It is yet another object of the present invention to provide an NMR well logging apparatus which includes selectable RF pulse frequencies to generate NMR measurements at a plurality of preselected radial distances into the earth formation from the axis of the tool.

SUMMARY OF THE INVENTION

The present invention is a nuclear magnetic resonance sensing apparatus. The apparatus comprises a magnet for generating a static magnetic field in a first region containing materials which are to be analyzed. The magnet generates substantially zero static magnetic field within a second region. The magnet has generally homogeneous magnetization along a longitudinal axis and is magnetized substantially perpendicular to the longitudinal axis. The apparatus also includes means for generating a radio frequency magnetic field within the first region for exciting nuclei of the materials which are to be analyzed. The means for generating the radio frequency magnetic field is disposed within the second region. The apparatus includes receiving means for receiving a nuclear magnetic resonance signal from the excited nuclei. The means for receiving also provides an output indicative of properties of the materials which are to be analyzed.

In a preferred embodiment of the invention, the means for generating and receiving comprise an antenna which is at least partially disposed within the second region.

In a specific embodiment of the invention, the antenna includes wire coils which are wound in planes substantially perpendicular to the longitudinal axis of the magnet. A high magnetic permeability ferrite is included inside the wire coils to increase efficiency of the antenna. The antenna includes a frequency control coil wound around the ferrite to change the magnetic permeability of the ferrite, thereby changing the tuning frequency of the antenna.

BRIEF DESCRIPTION OF THE DRAWINGS

FIG. 3 shows a sectional view of the detailed drawing of FIG. 2.

FIG. 10 shows an arrangement for a high vertical resolution antenna for the present invention.

FIG. 12 shows an alternative embodiment of the invention including an arrangement of the magnet, transceiver coil and additional receiver coil for use in very large diameter wellbores.

FIG. 13 shows a horizontal cross-section of the arrangement shown in FIG. 12.

DESCRIPTION OF THE PREFERRED EMBODIMENT

1. Configuration of the Apparatus

Figure 1:
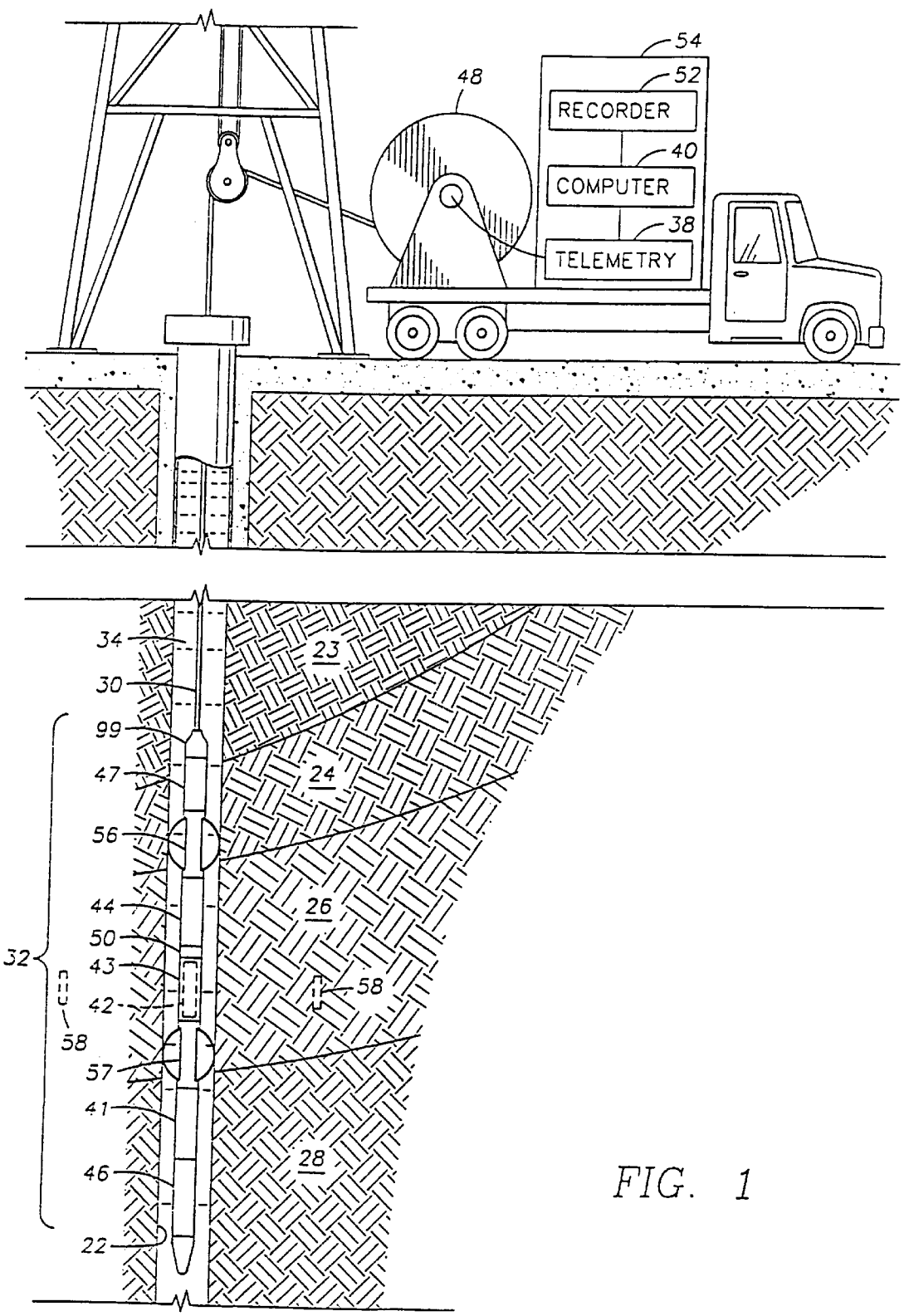
FIG. 1 shows a nuclear magnetic resonance (NMR) well logging apparatus disposed in a wellbore penetrating earth formations.

FIG. 1 shows a well logging apparatus disposed in a wellbore 22 penetrating earth formations 23, 24, 26, 28 for making measurements of properties of the earth formations 23, 24, 26, 28. The wellbore 22 in FIG. 1 is typically filled with a fluid 34 known in the art as "drilling mud". A "sensitive volume", shown generally at 58 and having generally cylindrical shape, is disposed in one of the earth formations, shown at 26. The sensitive volume 58 is a predetermined portion of the earth formations 26 in which nuclear magnetic resonance (NMR) measurements are made, as will be further explained.

A string of logging tools 32, which can include an NMR apparatus according to the present invention, is typically lowered into the wellbore 22 by a means of an armored electrical cable 30. The cable 30 can be spooled and unspooled from a winch or drum 48. The tool string 32 can be electrically connected to surface equipment 54 by an insulated electrical conductor (not shown separately in FIG. 1) forming part of the cable 30. The surface equipment 54 can include one part of a telemetry system 38 for communicating control signals and data to the tool string 32 and computer 40. The computer can also include a data recorder 52 for recording measurements made by the apparatus and transmitted to the surface equipment 54.

An NMR probe 42 according to the present invention can be included in the tool string 32. The tool string 32 is preferably centered within the wellbore 22 by means of a top centralizer 56 and a bottom centralizer 57 attached to the tool string 32 at axially spaced apart locations. The centralizers 56, 57 can be of types known in the art such as bowsprings.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42. The function of the probe 42 will be further explained.

Other well logging sensors (not shown separately for clarity of the illustration in FIG. 1) may form part of the tool string 32. As shown in FIG. 1, one additional logging sensor 47 may be located above the NMR electronics cartridge 44. Other logging sensors, such as shown at 41 and 46 may be located within or below the bottom centralizer 57. The other sensors 41, 46, 47 can be of types familiar to those skilled in the art and can include, but are not limited to, gamma ray detectors, formation bulk density sensors or neutron porosity detectors. Alternatively, parts of the NMR electronics may be located within electronic cartridges which form part of other logging sensors. The locations of the other sensors 41, 46, 47 shown in FIG. 1 are a matter of convenience for the system designer and are not to be construed as a limitation on the invention.

Figure 2:
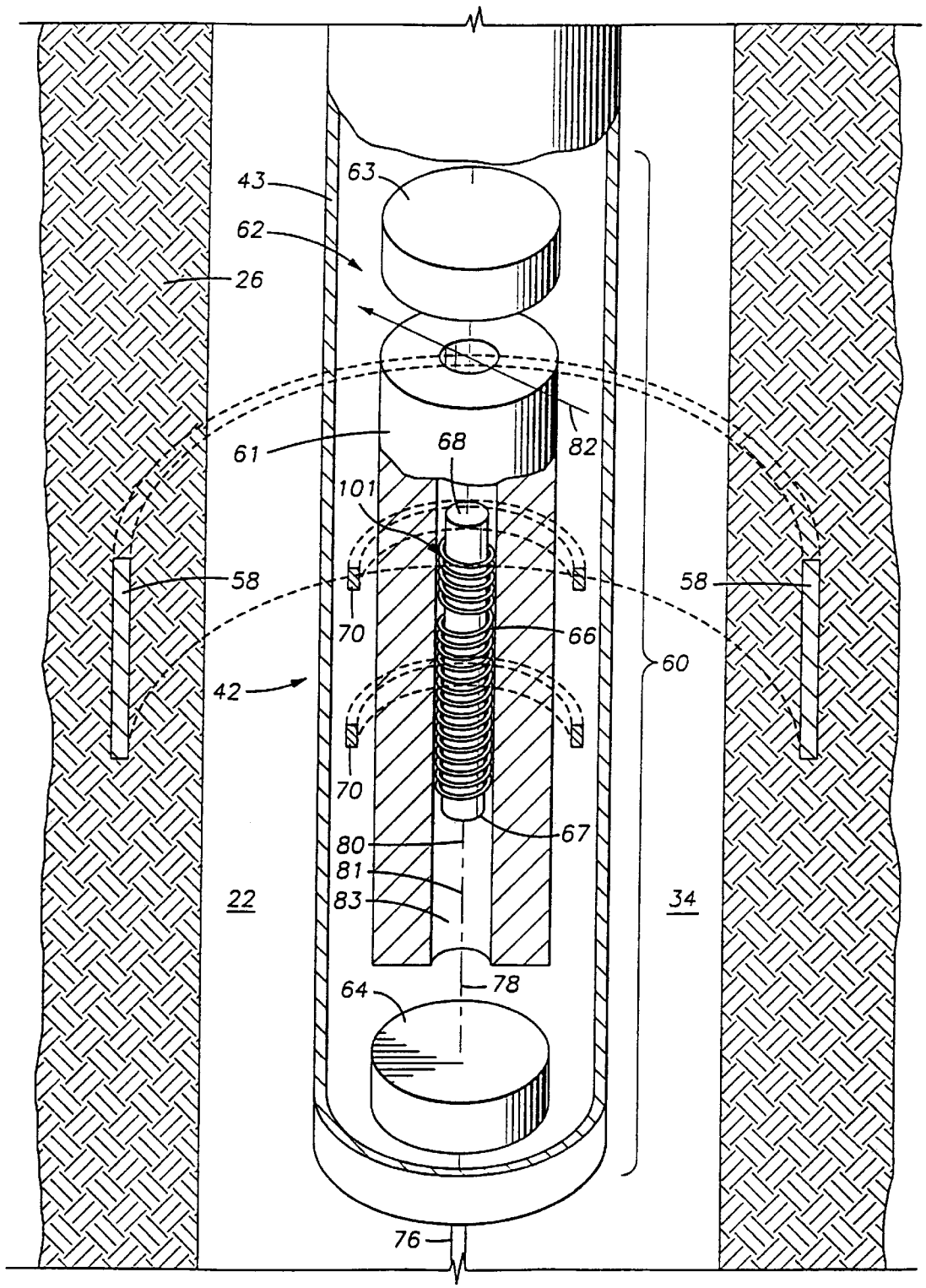
FIG. 2 shows the NMR probe of the apparatus of FIG. 1 in more detail.

FIG. 2 shows the NMR probe 42 in more detail. The NMR probe 42 preferably comprises a generally cylindrical, permanent- or electro- magnet assembly 60. The magnet assembly 60 can include at least one permanent magnet 62, which preferably has a substantially circular cross section and is generally elongated along a magnet axis 80. The magnet axis 80 is preferably positioned coaxially with the longitudinal axis 76 of the wellbore (22 in FIG. 1). Alternatively, a plurality of permanent magnets may be used to make up the magnet assembly 60. For clarity of the description of the invention, the one or more permanent magnets 62 will be considered together and referred to as permanent magnet 62, and their common axis 80 and the collocated axis of the wellbore (22 in FIG. 1) will be jointly identified herein as the longitudinal axis, shown at 78.

The permanent magnet 62 preferably has substantially uniform magnetization along the longitudinal axis 78. The direction 82 of magnetization of the magnet 62, shown at 82 is preferably perpendicular to the longitudinal axis 78. The permanent magnet 62 should have an overall length along the longitudinal axis 78 which is greater than twice the dimension of the permanent magnet 62 perpendicular to the longitudinal axis 78. The overall length of the permanent magnet 62 should also generally be greater than twice the diameter of the sensitive volume 58, as will be further explained.

The permanent magnet 62 preferably comprises a main permanent magnet 61, a top end magnet 63 located above the main permanent magnet 61 and a bottom end magnet 64 located below the main permanent magnet 61. The end magnets 63, 64 are provided to reduce axial asymmetry of the static magnetic field generated by the permanent magnet 62 within the sensitive volume 58.

The main permanent magnet 61 is preferably formed into an annular cylinder having a hole 83 of substantially circular cross section. The axis 81 of the magnet hole 83 is preferably parallel to the longitudinal axis 78. Details of the static magnetic field imparted by the permanent magnet 62 within the sensitive volume 58 and within the magnet hole 83 will be further explained. It is to be understood that the cylindrical shape of the permanent magnet 62 and the hole 83 are preferred but not essential. An essential feature of the magnet 62 is that the direction of the static magnetic field induced by the magnet 62 be substantially perpendicular to the longitudinal axis 78 within the sensitive volume 58. If the shape of the magnet 62 is other than cylindrical, for example, elliptical, the hole 83 should have the same general shape and the same ratio of long axis to short axis as the magnet 62 in order that the static magnetic field inside the hole 83 be substantially equal to zero, as will be further explained.

The main permanent magnet 61 can be made from a ferrite magnet material such as that sold under the trade name "Spinalor" and manufactured by Ugimag, 405 Elm St., Valparaiso, Ind., or another material sold under the trade name "Permadure" and manufactured by Philips, 230 Duffy Ave., Nicksville, N.Y. The permanent magnet material of the main permanent magnet 61 should be electrically nonconductive, so that an antenna used to generate a radio frequency magnetic field can be located in the hole 83, as will be further explained.

The top end magnet 63 and the bottom end magnet 64 may be formed from the same or similar ferrite permanent magnet material as is the main permanent magnet 61. Alternatively, the end magnets 63, 64 may be formed form magnetically stronger material such as a neodymium-iron-boron magnet alloy sold under the trade name "Ugistab" and manufactured by Ugimag, 405 Elm St., Valparaiso, Ind., or another material sold under trade name "Vacodym" and manufactured by Vacuumschmelze GMBH, 9/7 Rhenaniastrasse St., Berlin, Germany. Alternatively, the top end magnet 63 and the bottom end magnet 64 may be formed from samarium-cobalt permanent magnet material such as one sold under trade name "Recoma" and manufactured by Ugimag, 405 Elm St., Valparaiso, Ind., or another sold under trade name "EEC" and manufactured by Electron Energy Corp., 924 Links Ave., Landsville, Pa. The material forming the top end magnet 63 and the bottom end magnet 64 need not be electrically non-conductive.

The NMR probe 42 further includes the previously described transceiver antenna 67, which can comprise one or more coil windings 66 preferably arranged inside the hole 83 in the main permanent magnet 61. The coil windings 66 are preferably arranged so that each coil winding 66 lies substantially in a plane perpendicular to the longitudinal axis 78. Radio frequency alternating current passing through the coil windings 66 generates an RF magnetic field in the earth formation 26 in FIG. 1). The RF magnetic field generated by the current flow in the coil windings 66 has field directions substantially parallel to the longitudinal axis 78 within the sensitive volume 58.

The coil windings 66 have should have an overall length parallel to the longitudinal axis 78 which is about equal to the diameter of the sensitive volume 58. The overall length of the coil windings 66 parallel to the longitudinal axis 78 should also be substantially shorter than the overall length of the main permanent magnet 62 along the longitudinal axis 78, as will be further explained.

Preferably, the coil windings 66 are formed around a soft ferrite rod 68. The soft ferrite rod 68 can be formed from a material such as one sold under trade designation "F6" and manufactured by MMG-North America, 126 Pennsylvania Ave., Paterson, N.J., or another material sold under trade designation "3C2" and manufactured by Philips, 230 Duffy Ave., Nicksville, N.Y. The ferrite rod 68 preferably is positioned parallel to the longitudinal axis 78. The overall length of the ferrite rod 68 along the longitudinal axis 78 should be substantially less than the length of the permanent magnet 62 along the longitudinal axis 78. Alternatively, a plurality of coils and a plurality of ferrite rods may be employed. The assembly of coil windings 66 and soft ferrite rod 68 will be referred to hereinafter as the transceiver antenna 67. The ferrite rod 68 has the particular function of increasing the field strength of the RF magnetic field generated by the transceiver antenna 67. Using the ferrite rod 68 particularly enables the transceiver antenna 67 to have a relatively small external diameter so that it can be located in the hole 83. Having a small external diameter particularly enables the transceiver antenna 67 of the present invention to be sized so that the apparatus of the present invention can be used in smaller diameter wellbores.

The transceiver antenna 67 also can include a frequency control coil 101, which can be another wire coil wound around the ferrite rod 68. As will be further explained, a control voltage selectable by the system operator can be applied to the frequency control coil 101 to change the resonant frequency of the transceiver antenna 67. The purpose of changing the resonant frequency, and the source of the control voltage will be further explained.

The NMR probe 42, can also comprise one or more additional receiver coils, such as the one shown generally at 70 (only the lead-in wires are shown in FIG. 2 for clarity) which are arranged about the exterior surface of the permanent magnet 62. Each turn (not shown in FIG. 2) of additional receiver coil 70 should lie in a plane substantially parallel to a plane containing both the magnetization axis 82 of the permanent magnet 62 and containing the longitudinal axis 78. Preferably the additional receiver coil 70 has an overall length parallel to the longitudinal axis 78 which is less than the overall length of the transceiver antenna 67. As a consequence, the overall length of the additional receiver coil 70 parallel to the longitudinal axis 78 should be substantially shorter than the length of the permanent magnet 62 along the longitudinal axis 78. Alternatively, a plurality of additional receiver coils 70 may be included in the NMR probe 42. A particular property of the additional receiver coil 70 arranged as described herein is that it is substantially orthogonal to, and consequently substantially insensitive to, the direct RF magnetic field generated by the transceiver antenna 67. This insensitivity to the direct RF field enables the additional receiver coil 70 to provide the apparatus of the present invention with very short "dead time", while the current flowing through the transceiver antenna 67 decays to zero, as will be further explained.

Details of the synthesis of the RF magnetic field in the sensitive volume 58 using the transceiver antenna 67, and details of detecting an induced NMR signal using the transceiver antenna 67 and/or the additional receiver coil 70 will be further explained.

The permanent magnet 62, the transceiver antenna 67 and the additional receiver coil 70 are preferably housed within a non-conductive, non-ferromagnetic protective housing 43. Such housings and additional components (not shown) for excluding the drilling mud under high hydrostatic pressure, are familiar to those skilled in the art.

Figure 4:
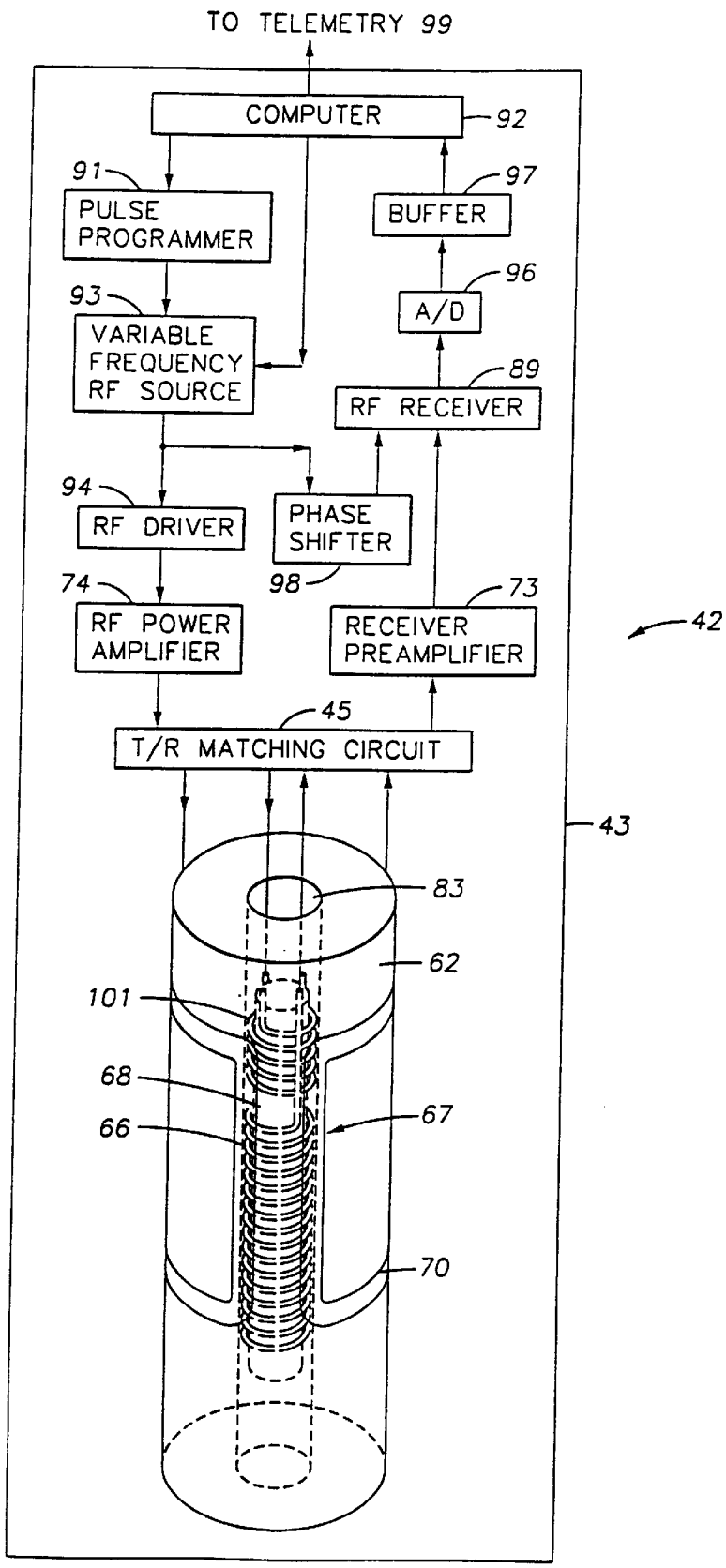
FIG. 4 shows a functional block diagram of the NMR apparatus of the invention.

FIG. 4 shows, in general form, the NMR probe 42 and a functional block diagram of the NMR well logging apparatus according to the present invention. A transmitter/receiver (T/R) matching circuit 45 can be disposed within the housing 43. The T/R matching circuit 45 typically includes a series of resonance capacitors (not shown separately), a transmitter/receiver switch (not shown separately) and both "to-transmitter" and "to-receiver" matching circuitry. The T/R matching circuit 45 can be coupled both to a radio frequency (RF) power amplifier 74 and to a receiver preamplifier 73. While shown as located inside the housing 43 the T/R matching circuit 45, the RF power amplifier 74 and the receiver preamplifier 73 alternatively may be located outside the housing 43 within the top centralizer (56 in FIG. 1) or within the NMR electronics cartridge (44 in FIG. 1). The locations of the T/R matching circuit 45, the RF power amplifier 74 and the receiver preamplifier 73 are not to be construed as a limitation on the invention.

Part of the control circuitry for the NMR logging apparatus includes a down-hole computer 92, which among other functions provides control signals to a pulse programmer 91. The computer 92 and the pulse programmer 91 may also be located within the top centralizer 56 or in the NMR electronics cartridge 44. The pulse programmer 91 controls the timing and operation of the variable frequency RF signal source 93. The RF driver 94 receives an input from the variable frequency RF source 93 and provides an output to the RF power amplifier 74. The RF power amplifier 74 provides a high power signal to drive the transceiver antenna 67 for generating an RF magnetic field in the sensitive volume (58 in FIG. 1). The RF power amplifier 74 can be electrically connected (typically by the switch in the T/R matching circuit 45) to the transceiver antenna 67 during transmission of RF power pulses.

During reception of the induced NMR signal, the transceiver antenna 67 and/or the additional receiver antenna 70 can be electrically connected to the receiver preamplifier 73 by means of the switch in the T/R matching circuit 45. The output of the RF receiver preamplifier 73 is provided to an RF receiver 89. The RF receiver 89 also receives a phase reference input from a phase shifter 98. The phase shifter 98 receives a primary phase reference input from the variable frequency RF source 93. The RF receiver 89 may include quadrature detection. The RF receiver 89 provides an output to an A/D converter 96. The A/D converter 96 output can be stored in a buffer 97 until required for use by the down-hole computer 92. Alternatively, the buffer 97 contents can be conducted directly to a downhole part of the telemetry unit 99 for transmission to the surface equipment (54 in FIG. 1).

The downhole computer 92 typically preprocesses the data from the buffer 97 and transfers the preprocessed data to the downhole portion of the telemetry system, shown generally at 99. The downhole portion of the telemetry system 99 transmits the preprocessed data to the telemetry unit (38 in FIG. 1) in the surface equipment (54 in FIG. 1). The telemetry unit 38 transfers the data to the surface computer (40 in FIG. 1) for calculating and presenting desired well logging output data for further use and analysis as is understood by those skilled in the art.

All of the elements described herein and as shown in FIG. 4, except the transceiver antenna 67, the magnet assembly (60 in FIG. 2) and the additional receiver antenna 70, at the convenience of the system designer may be disposed within the housing 43, the top centralizer (56 in FIG. 1) or the NMR electronics cartridge (44 in FIG. 1). These same elements may alternatively be located at the earth's surface, for example in the surface equipment 54 using the cable (30 in FIG. 1) for transmission of electrical power and signals to the transceiver antenna 67 and the additional receiver antenna 70.

Figure 5:
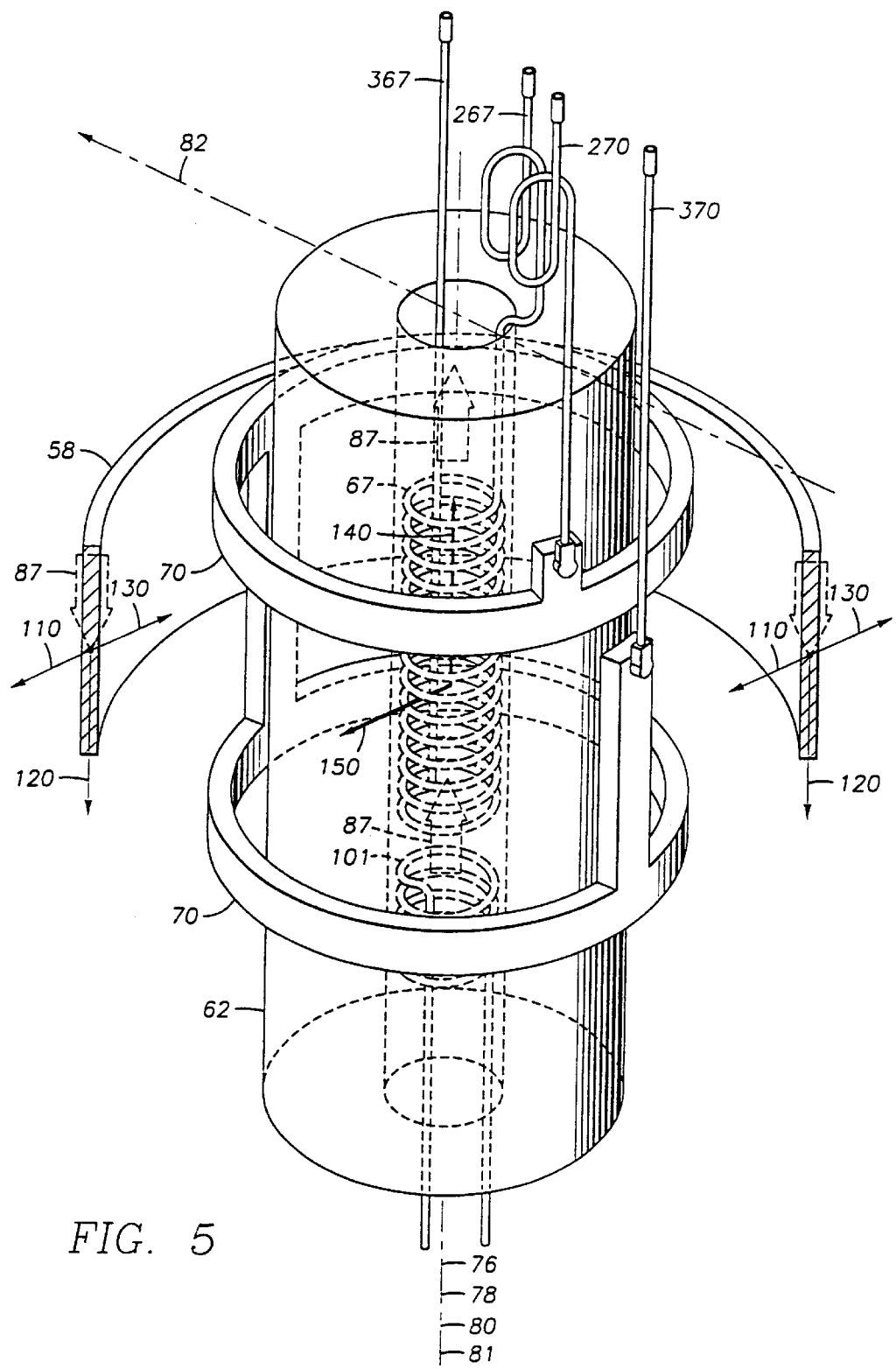
FIG. 5 shows a graphic representation of the static and radio frequency (RF) magnetic fields of the apparatus of the present invention.

FIG. 5 illustrates the static magnetic field and the RF magnetic field created by the NMR well logging apparatus of the present invention. The direction of the static magnetic field generated by the permanent magnet (62 in FIG. 2) is shown by arrows 110. Nuclear magnetic moments in the material to be analyzed (the earth formation located within the sensitive volume 58) are substantially aligned in the direction of the static magnetic field. In the preferred embodiment of the invention, the direction of the RF magnetic field, denoted by arrows 120, within the sensitive volume 58 is substantially perpendicular to the static magnetic field at any point within the sensitive volume 58. Such a magnetic field arrangement is conventional for NMR experiments.

Although the static magnetic field direction is not symmetrical about the longitudinal axis 78 (the field direction undergoes two rotations for each circumlocution of the longitudinal axis 78), the static magnetic field magnitude is symmetric about the longitudinal axis 78. The static magnetic field has an amplitude gradient which is also symmetrical about the longitudinal axis 78 and is directed substantially radially inwardly towards the longitudinal axis 78. As a result there is generally only one substantially cylindrical surface external to the permanent magnet 62 which has a particular static magnetic field amplitude (ignoring end effects of the magnet). It follows from this particular feature of the static magnetic field that stray resonance signals from diverse materials such as the drilling mud (34 in FIG. 1), which originate outside of the sensitive volume 58 do not seriously affect the NMR measurements if appropriate RF frequencies are selected.

As previously explained, the transceiver antenna 67 can include the frequency control coil 101. A DC voltage having a magnitude selectable by the system operator can be applied to the frequency control coil 101 to partially magnetize the ferrite rod 68. Circuitry for providing the selectable DC voltage to the frequency control coil 101 is well known in the art and is not shown in FIG. 5 for clarity of the illustration. The DC source (not shown) can be directly controlled by the system operator, or can be controlled by the down hole computer (92 in FIG. 4) in response to, among other things, the radial depth at which the sensitive volume (58 in FIG. 2) is positioned. Changes in the radial depth of the sensitive volume 58 can occur, for example, as a result of environmental changes in the static magnetic field induced by the magnet (62 in FIG. 2). Partially magnetizing the ferrite rod 68 changes its magnetic permeability, and as a consequence, changes the inductance of the transceiver antenna 67. Changing the inductance of the transceiver antenna 67 changes its resonant frequency so that it can be tuned to nearly any frequency within a wide range. The RF power pulse generated by the RF source 93 and the RF power amplifier 73 can then be efficiently converted by the transceiver antenna 67 into a strong RF magnetic field within the sensitive volume 58. As is understood by those skilled in the art, because the static magnetic field has a non-zero magnitude gradient with respect to radial distance from the longitudinal axis 78, changing the RF field frequency will change the radius of the sensitive volume 58. A particular advantage of the using the control coil 101 according to the present invention is the ability to change the RF frequency very easily while substantially maintaining the amplitude distribution of the RF field.

Undesired static magnetic field end effects may be substantially eliminated by making the transceiver antenna 67 somewhat shorter along the longitudinal axis 78 than the permanent magnet 62, so as not to excite materials at the extreme longitudinal ends of the static magnetic field. To reduce the required length of the permanent magnet 62, the end magnets 63 and 64 may be utilized, as previously explained.

When RF power pulses are conducted through the transceiver antenna 67, the antenna 67 generates an RF equivalent magnetic dipole 87 centered at the origin and directed along the longitudinal axis 78. The equivalent magnetic dipole 87 generates an RF magnetic field of substantially equal amplitude within the sensitive volume 58, directed opposite to the dipole direction. Since the RF magnetic field direction is parallel to the longitudinal axis 78, the bulk nuclear magnetization, denoted in FIG. 5 by arrows 130, at any point in the sensitive volume 58 rotates in planes perpendicular to the longitudinal axis 78. The free precession of the nuclear magnetic moments, however, is around the static magnetic field direction at any point within the sensitive volume 58, and the free precession is always in phase along the longitudinal axis 78. The free precession will therefore induce an RF signal in the transceiver antenna 67. The induced magnetic moment in the transceiver coil 67 is shown in FIG. 5 as arrows 140.

Those skilled in the art of nuclear magnetic resonance measurements will readily comprehend that the free precession of the bulk nuclear magnetization about the static magnetic field will also induce an RF signal in the additional receiver coil 70, this signal shown in FIG. 5 as arrows 150. The signal induced in the additional receiver coil 70 is directionally rotated 90 degrees (orthogonal) with respect to the signal which is induced in the transceiver coil 67. Because the transceiver coil 67 is substantially orthogonal to the additional receiver coil 70, during transmission of the RF pulse, there is substantially zero signal directly induced the additional receiver coil 70. As a result, the dead time of the whole receiving system may be reduced significantly with respect to prior art NMR apparatus having only a single transceiver antenna.

Figure 3A:
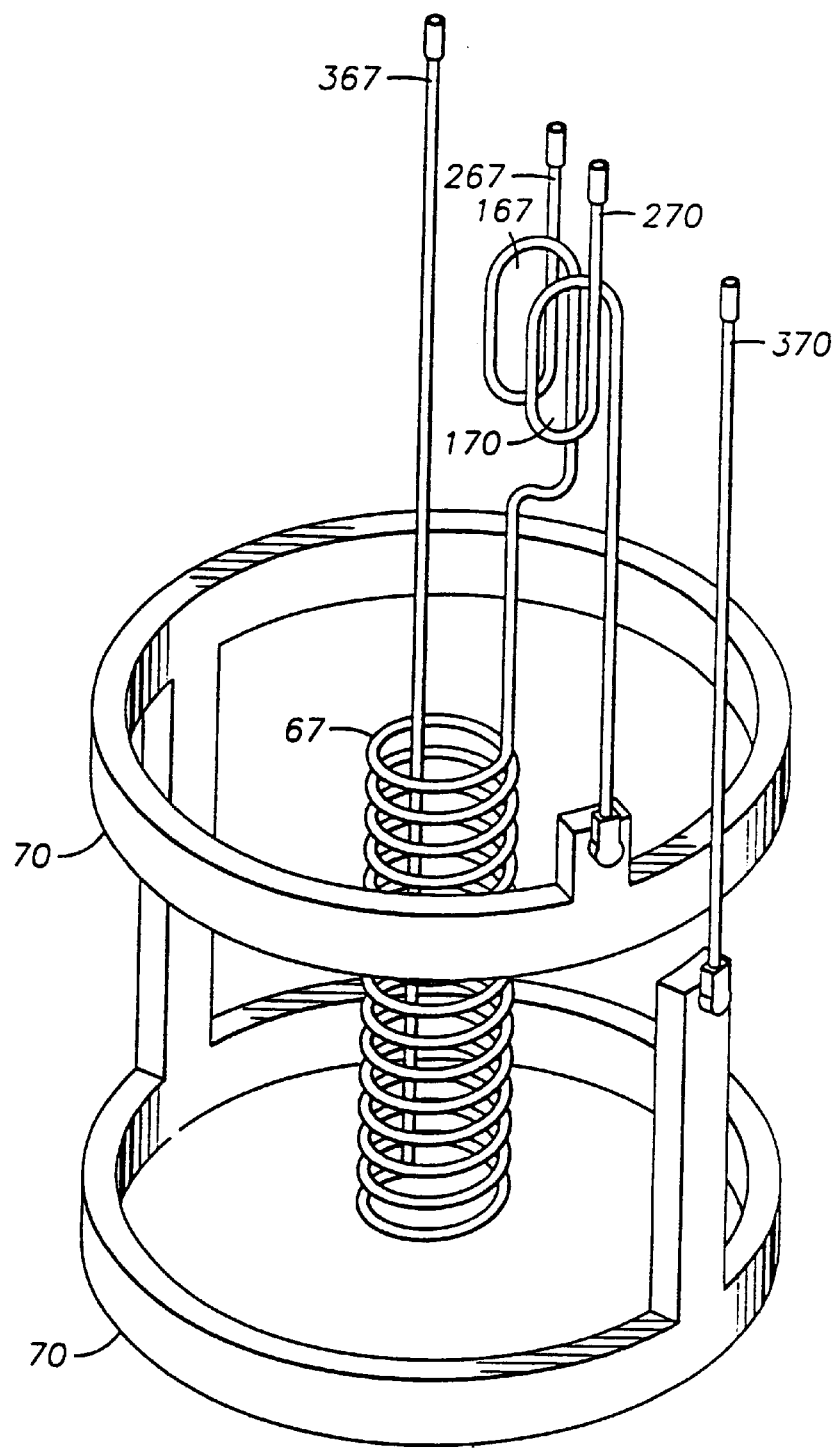
FIG. 3A shows additional wire coils used to cancel mutual inductance between the transceiver antenna and the additional receiver coil as shown in FIG. 3.

FIG. 3A shows an embodiment of the transceiver antenna 67 and the additional receiver 70 which further improves the performance of the apparatus of the present invention. The transceiver antenna 67 includes lead-in wires 267 and 367 which are connected, as previously explained to the T/R matching circuit (45 in FIG. 4). Similarly the additional receiver coil 70 includes lead-in wires 270 and 370 to connected to the T/R matching circuit 45. Small wire loops, shown generally at 167 and 170 can be positioned, respectively, in either of the lead in wires for the transceiver antenna 67 and the additional receiver coil 70. The wire loops 167, 170 are preferably adjusted by passing RF current through the transceiver antenna 67 while observing the voltage on the additional receiver coil 70. The wire loops 167, 170 should be adjusted to substantially eliminate any voltage being induced in the additional receiver coil 70 by the current passing through the transceiver antenna 67. The step of adjusting the wire loops 167, 170 is preferably performed while the NMR probe 42 is suspended in air.

Orthogonal transmission and reception of the RF signals has an additional advantage when permanent magnets are employed and the system dead time has to be as short as possible. Prior art NMR logging tools typically suffer high levels of magnetoacoustic and magnetostrictive ringing. The means by which the present invention reduces such ringing will be further explained.

Another particular advantage of the present invention is the presence of a substantially constant static magnetic field amplitude and static field amplitude gradient in the materials to be analyzed within the sensitive volume 58. This feature can be used for direct measurement of the diffusion coefficient of liquid present in the material to be analyzed, as explained for example in C. P. Slichter, *Principles of Magnetic Resonance,* Appendix G, Springer Verlag Berlin Heidelberg, N.Y., 1980. The amplitude gradient of the static magnetic field can be used to generate a diffusion measurement particularly by adjusting the frequency of the RF magnetic field, as previously explained, to first generate the sensitive volume 58 where the static magnetic field has a gradient which exceeds internal magnetic field gradients of the materials to be analyzed. A static field gradient which will perform according to this aspect of the invention can be about 30 Gauss/cm. The NMR signal can be received from this same sensitive volume 58 at the same frequency. The sensitive volume 58 can then be moved by adjusting the RF magnetic field frequency to be positioned where the static magnetic field is generally less than the internal gradients in the materials to be analyzed, generally corresponding to a static field gradient of about 5 Gauss/cm.

The gradient of the static magnetic field can also be utilized to perform radial fluid flow measurements by exciting the nuclei using RF pulses having a first frequency, and receiving the induced NMR signal at a second frequency. This is equivalent to exciting the nuclei at one radial distance from the wellbore 22 and receiving the signal therefrom at another radial distance from the wellbore 22.

2. Design Parameters for the Preferred Embodiment

In the preferred embodiment of the invention, the signal-to-noise ratio (S/N) for the NMR measuring process is sought to be optimized. The following discussion is intended to explain how certain principal parameters affect the S/N. The principal parameters typically include the geometries of the permanent magnet (62 in FIG. 2) and the transceiver antenna (67 in FIG. 2), the power of radio frequency (RF) pulses used to energize the transceiver antenna 67, and the quality factor of the transceiver antenna 67.

Using the transceiver antenna 67 constructed as previously described in the present embodiment of the invention, the magnitude of an NMR signal, S, induced in the transceiver antenna 67 is typically related to the magnitude of an RF electromagnetic field, $B_1$, by the Reciprocity Theorem and can be described as in the following expression:

$$S = w\, m\, A_{sv}(B_1/I_1)l \quad (1)$$

where m and $A_{sv}$, respectively, represent the nuclear magnetization and the cross sectional area of the sensitive volume (58 in FIG. 1), $I_1$ represents the magnitude of the current flowing in the transceiver antenna 67, the oscillating frequency of the current is represented by w and l represents the effective length of the transceiver antenna 67. For simplicity of the discussion, m and $B_1$ are assumed to be substantially homogeneous within the sensitive volume 58.

By substituting $m = x\, B_0/\mu_0$; where x represents the nuclear magnetic susceptibility of hydrogen nuclei within the sensitive volume 58, $w = y\, B_0$, where $B_0$ represents the static magnetic field generated by the permanent magnet (62 in FIG. 2) and described in equation (1), it is therefore possible to derive the following expression for S:

$$S = (y\, x/\mu_0) B_0^2 (B_1/I_1) A_{sv} l \quad (2)$$

The NMR signal thus acquired is therefore directly proportional to the sensitive volume 58 in the earth formation (26 in FIG. 1). The geometry of the sensitive volume 58 is determined by the existence of a resonance condition. In pulsed NMR, the resonance condition is typically met when the deviation of the static magnetic field magnitude $B_0(R)$ from its value $B_0(R_{sv})$, corresponding to the central frequency of the current energizing the transceiver antenna 67 ($B_0(R) = w/y$), is no greater then half the magnitude of the RF magnetic field $B_1$ induced by passing current through the transceiver antenna 67, expressed as shown in equation (3):

$$B_0(R) - B_0(R_{sv}) \leq B_1/2 \quad (3)$$

The static magnetic field $B_0(R)$ at the excitation radius $R_{sv}$ may also be described in the form of a Taylor expansion as:

$$B_0(R) = B_0(R_{sv}) - (\partial B_0/\partial R)(R - R_{sv}) \quad (4)$$

where $(\partial B_0/\partial R)$ represents the static magnetic field gradient at radius $R = R_{sv}$. From equation (3):

$$B_0(R_0) - B_0(R_i) \leq B_1 \quad (5)$$

where $R_0$ and $R_i$ represent, respectively, the outer and inner radii of the sensitive volume 58. As a practical matter $R_0 - R_i \ll R_{exc}$.

$$A_{sv} = 2\pi R_{sv} B_1/(\partial B_0/\partial R) \quad (6)$$

$$B_0 = A_m B_r / 2\pi R_{sv}^2 \quad (7)$$

where $A_m$ represents the permanent magnet 62 cross sectional area. From equations (6) and (7):

$$A_{sv} = (B_1/B_0) \pi R_{sv}^2 \quad (8)$$

The current flowing in the transceiver antenna 67 may be expressed as $I_1 = (P_1/r)^{1/2}$, where $P_1$ represents the peak power of the RF pulse energizing the antenna 67, r represents the active part of the antenna 67 impedance. Therefore: $r = w\, L/Q = y\, B_0 L/Q$. Substituting for equation (2) yields the expression:

$$S = (\pi X/\mu_0)(y\, B_0)^{1/2}(P_1 Q/L)^{1/2}(B_1/I_1)^2 R_{sv}^2 l \quad (9)$$

As is understood by those skilled in the art, the root-mean-square (RMS) thermal noise can be described by the expression:

$$N_{rms}=(4kT\Delta fr)^{1/2} \tag{10}$$

where $\Delta f$ represents the receiver bandwidth. The bandwidth is typically about $y\,B_1/2\pi$ for a matched receiver; k represents Boltzmann's constant; and T represents the absolute temperature.

Then substituting for equations (9) and (10) yields the following expression for S/N:

$$S/N=[(2kT)^{-1/2}\pi^{3/2}(X/\mu_0)(B_0/y)^{1/4}R_{sv}^2][(B_1/I_1)^{3/2}P_1^{1/4}(Q/L)^{3/4}l] \tag{11}$$

The first bracketed expression in equation (11), for a given proton spin density and absolute temperature, depends only on the static magnetic field parameters and the radius of the sensitive volume 58. The second bracketed expression in equation (11) describes parameters used in the design of the transceiver antenna 67, as will be further explained.

Synthesis of the Radio Frequency Magnetic Field

The following description is provided to assist in developing the design parameters for the transceiver antenna (shown as 67 in FIG. 2). In the present description the transceiver antenna 67 can be described as a pair of magnetic charges placed at the ends of the transceiver antenna 67. The longitudinal component of an RF magnetic field generated in the center plane of the transceiver antenna 67, created by passing RF power through the transceiver antenna 67, can be described by the following expression:

$$B_1=q^m(l\,1/4\pi)/[R^2+(l/2)^2]^{3/2} \tag{12}$$

wherein $q^m=\mu_0\mu_{rod}(\pi d^2/4)I_1 n/l$. In equation (12), $q^m$ represents the effective magnetic charge, $\mu_0$ represents the magnetic permeability of free space, $\mu_{rod}$ represents the magnetic permeability of the ferrite rod (shown as 68 in FIG. 2); d represents the diameter of the ferrite rod 68, $I_1$ represents the current flowing in the transceiver antenna 67, n represents the number of coil turns in the transceiver antenna's 67 coil windings (66 in FIG. 2), l represents the transceiver antenna 67 length, and R represents the radius of the sensitive volume (shown as 58 in FIG. 2).

It is to be noted that the proportionality to antenna length (l) in equation (12) suggests improvement in S/N with respect to increasing l, until l is limited by the vertical resolution requirements of the apparatus.

In the absence of the ferrite rod 68 inside the antenna coil (66 in FIG. 2), $\mu_{rod}=1$, and for a fixed value of n:

$$B_1/I_1\,l^{-3}[1+(2R/l)^2]^{-3/2} \tag{13}$$

Without the ferrite rod (68 in FIG. 2) inside the transceiver antenna (67 in FIG. 2), the result indicated by equation (13) indicates that the transceiver antenna 67 would have low efficiency.

Figure 6:
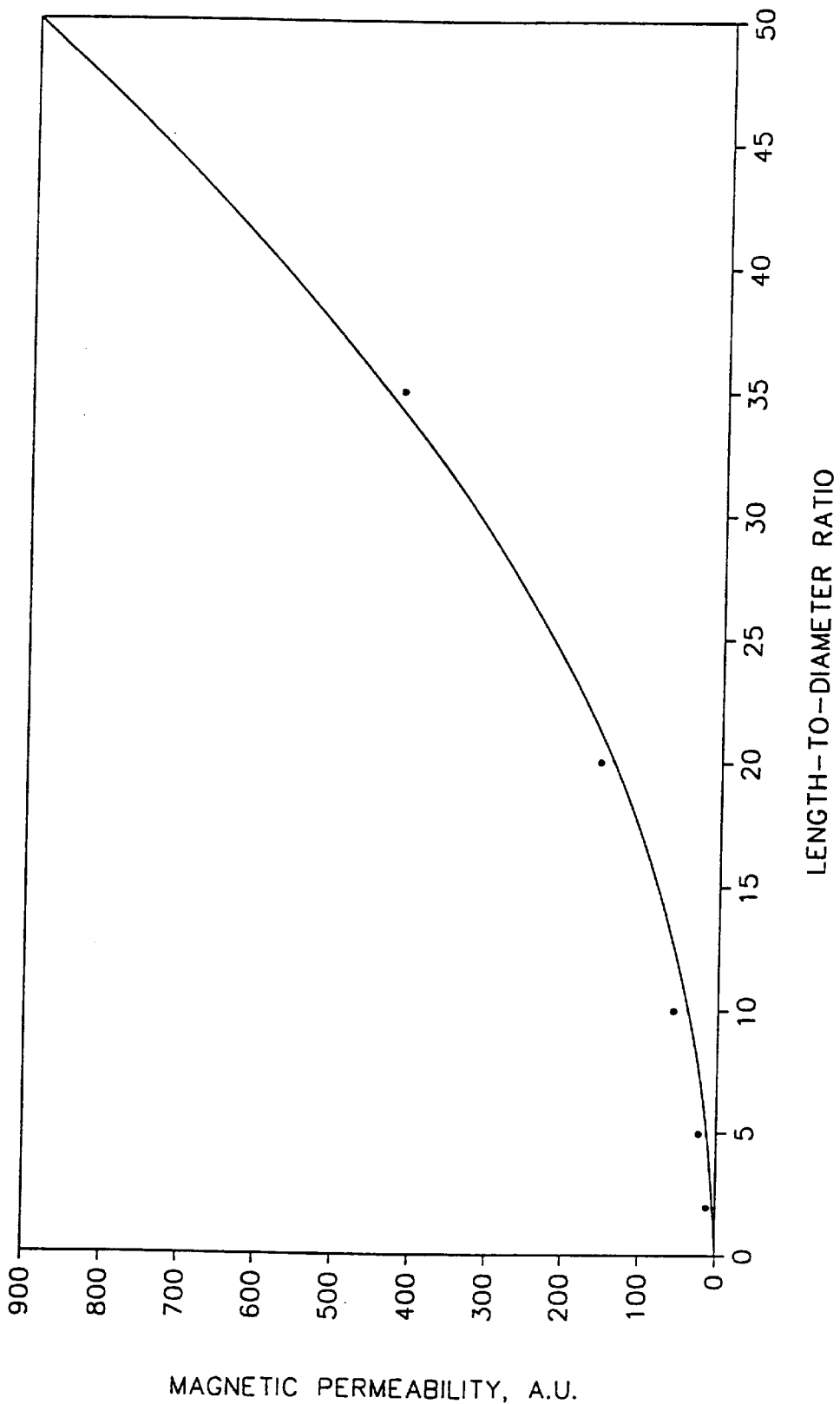
FIG. 6 shows a graph of correspondence between length-to-diameter ratio for an antenna of the present invention with respect to magnetic permeability of a ferrite rod in the antenna.
Figure 7:
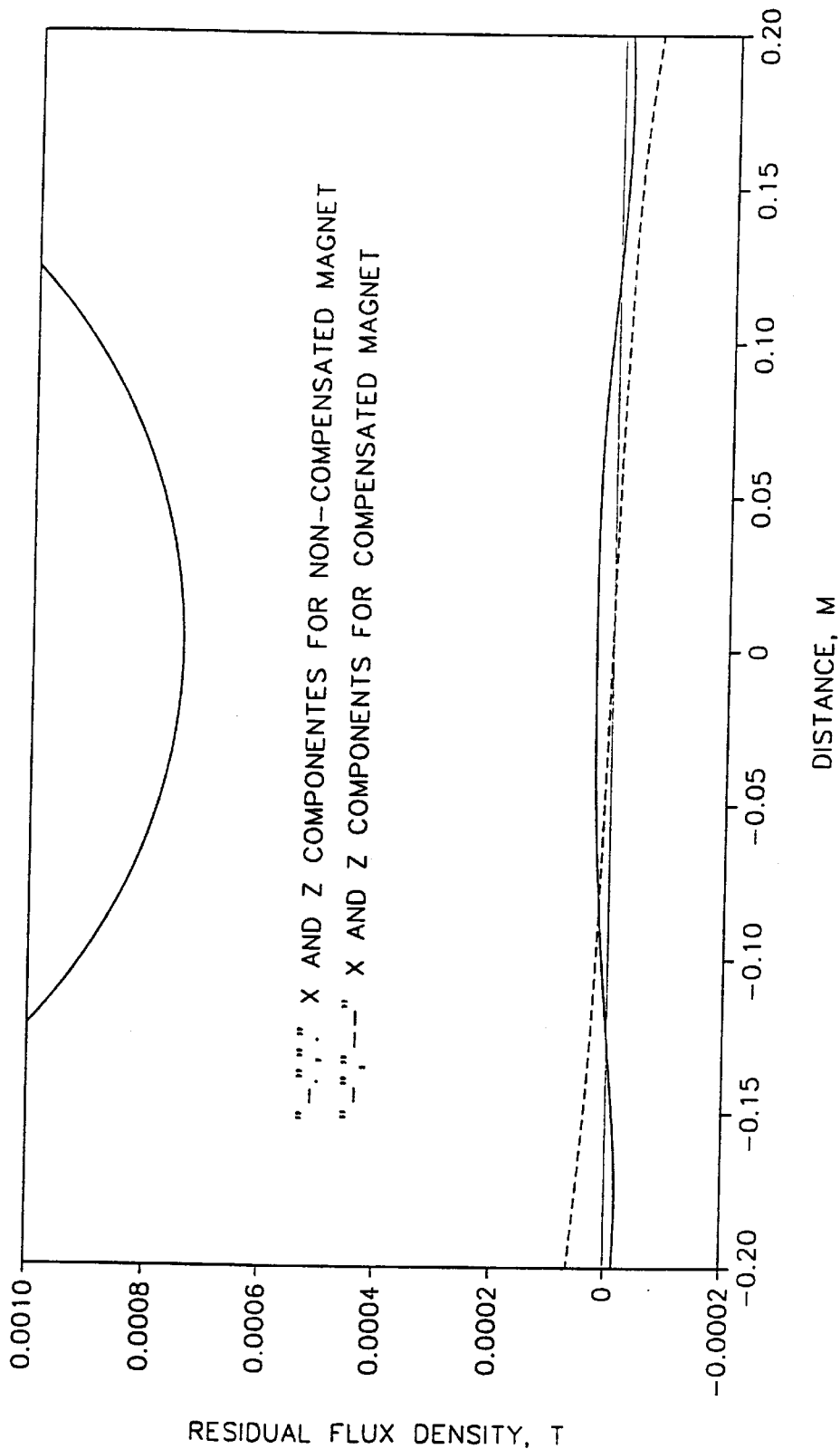
FIG. 7 shows a graph of the static magnetic field inside the magnet hole when end magnets are provided on the main magnet.

For a high permeability ($\mu$) ferrite rod 68 material, $\mu_{rod}$ is mainly determined by the length-to-diameter ratio of the transceiver antenna 67. For those skilled in the art it should be apparent that $\mu_{rod}\approx 1/D$, where D represents a "demagnetizing factor" of the ferrite rod 68. FIG. 6 shows in graphic form the dependence of $\mu_{rod}$ on the ratio of l/d, based on D values described by R. M. Bozort, "Ferromagnetism", D. Van Nostroud Company, Inc. New York, 1951. A simple approximation of this dependence for large length-to-diameter ratios can be described by the following expression:

$$\mu_{rod}\approx 0.35(l/d)^2 \tag{14}$$

Substituting for equation (12) yields the expression:

$$B_1/I_1\approx 0.18\mu_0 nl^{-1}[1+(2R/l)^2]^{-3/2} \tag{15}$$

The approximation shown in equation (15) demonstrates that the ratio $B_1/I_1$ is not dependent on d and the ratio has relatively constant values within a range for l comprising $2R<l<5R$. A weak maximum in the ratio occurs at $l=2\sqrt{2}R$. Because the aperture of the transceiver antenna 67 which is required for use in a well logging tool does not typically exceed a value of 5R, the reduction in RF field strength, expressed as $B_1/I_1$, with respect to increasing l, may be substantially neglected when the antenna 67 includes the ferrite rod 68. Such behavior of the antenna 67 makes the antenna 67 (referred to as a longitudinal dipole antenna) including the ferrite rod 68 similar in electromagnetic response to the transversal RF dipole antennas employed in the prior art, from the standpoint of signal accumulation by using an antenna of maximum possible length. A transversal dipole antenna, for comparison, is described in U.S. Pat. No. 4,710,713 issued to Taicher et al.

For a typical two-dimensional transversal RF dipole antenna as described in the Taicher et al '713 patent, supra, the ratio $B_1/I_1$ can be described by the following expression:

$$B_1/I_1=\mu_0 nR_a/4R^2 \tag{16}$$

where $R_a$ represents the transceiver antenna 67 dipole radius, which radius is primarily restricted to the radius of the wellbore (22 in FIG. 1).

It can be determined by reviewing equations (15) and (16) that the rate of reduction in the RF field strength for transverse dipole antenna is much greater than for the longitudinal dipole antenna (the transceiver antenna 67 in FIG. 2) according to the present invention. This gives the present invention the particular advantage of making possible NMR measurements at increased radial depth of investigation into the earth formation (26 in FIG. 1) over the prior art using the transversal dipole type antenna. Moreover, the RF magnetic field generated by the longitudinal dipole transceiver antenna (67 in FIG. 2) of the present invention, which includes the ferrite rod 68, is substantially independent of the diameter of the wellbore 22. By contrast, the RF magnetic field generated by a transverse dipole antenna, as in the prior art, depends linearly on $R_a$. The longitudinal dipole antenna (transceiver antenna 67 in FIG. 2) of the present embodiment of the invention is therefore particularly suitable for use in small diameter wellbores.

The inductance L of the coil windings (66 in FIG. 2) can be calculated from the expression: $L=\mu_0\mu_{rod}(\pi d^2/4)n^2/l$. Then substituting $\mu_{rod}$ as defined in equation (14) yields the expression for inductance:

$$L=(0.35\,\mu_0\pi/4)n^2 l \tag{17}$$

Substituting equations (17) and (5) into equation (16) yields the following expression for S/N:

$$S/N\,l^{-3/4}[1+(2R/l)^2]^{-3/4} \tag{18}$$

In the preceding discussion one simplifying assumption is that the Q of the transceiver antenna 67 does not depend on 1 of the transceiver antenna 67. Equation (18) typically has a maximum at $l=(2\sqrt{2.6})R_{sv}$ which should be taken into account in construction of the transceiver antenna 67 according to the present embodiment of the invention.

Referring once again to FIG. 2, the relative dimensions of the transceiver antenna 67 should be selected in order to optimize S/N. The ratio of antenna length l to the radius of the sensitive volume 58 should be in a range of approximately 3–5. The diameter of the ferrite rod 68 should no be so large as to ensure that $\mu_{rod} << \mu$. For typical values of $\mu$, which can be in the range from 1500–2000, the l/d ratio of the ferrite rod 68 should generally not exceed 40. The ferrite rod 68 diameter is approximately limited to the diameter of the hole 83 in the permanent magnet 62. It is also important to note that the diameter of the ferrite rod 68 should be as large as practical within the limits of the diameter of the hole 83 to minimize magnetic flux density in the ferrite rod 68 and consequently to minimize specific power loss (maximize the Q of the transceiver antenna 67) when the RF pulses are conducted through the transceiver antenna 67. Magnetization dynamics in ferrite materials causing power loss in oscillating fields are discussed, for example in A. Reiderman, *Magnetic Characterization of Recording Media,* UB Ac. Sc. USSR, Part 1, p. 37, 1990.

Figure 8:
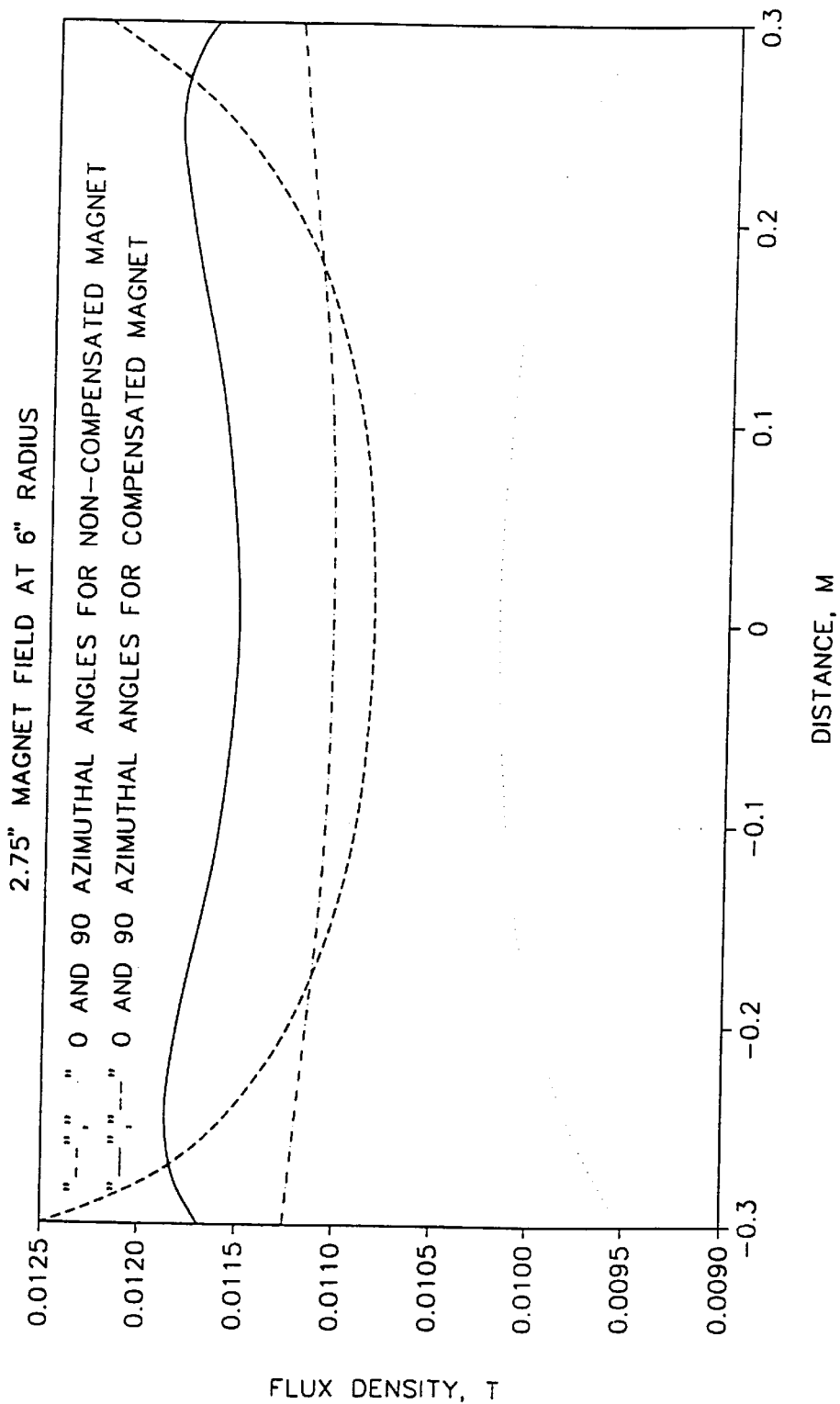
FIG. 8 shows a graph of the static magnetic field induced by the magnet in the sensitive volume when end magnets are provided on the main magnet.

The number of turns, n, used in the coil windings 66 is preferably selected to simplify transmitter/receiver matching. In the preferred embodiment of the invention wherein the apparatus (32 in FIG. 1) is to be used in a 6 inch diameter wellbore (22 in FIG. 1) and to have a 12 inch diameter sensitive volume 58, the ferrite rod 68 dimensions are typically 40 cm and 1.5 cm for l and for d, respectively, with 3 turns (n=3) on the coil 66. FIG. 8 shows a graphic representation of the RF field distribution at the radius of the sensitive volume 58 (this radius being about 6 inches).

Synthesis of the Static Magnetic Field

Referring once again to FIG. 2, the magnet assembly 61 including the magnet hole 83 are shown. The magnet assembly 61 also typically includes the end magnets 63 and 64. The magnet assembly 61 produces a substantial magnetic field within the sensitive volume 58, but produces substantially zero magnetic field inside the magnet hole 83, where the transceiver antenna 67 is preferably placed. The magnet assembly 61 prepolarizes nuclei in the formation (26 in FIG. 1) to ensure a steady state nuclear magnetization measurement even while the NMR probe 42 is moving through the wellbore (22 in FIG. 1).

Assuming first that the magnet assembly 61 is long enough so that end effects may be neglected, the magnetostatic analysis may be reduced to a two-dimensional problem. For those skilled in the art of magnetic field synthesis from permanent magnet sources, it should be apparent that there is substantially zero magnetic field inside a circular cylindrical hole in a circular cylindrical permanent magnet which is magnetized uniformly perpendicular to the cylindrical axis. For example, in Manlio G. Abele, *Structure of Permanent Magnets,* John Wiley & Sons, pp. 42–66, 1993 it is shown that the field inside a permanent magnet cylinder magnetized perpendicularly to its axis is uniform and is equal to $B_r/2$, where $B_r$ represents the remanence magnetization of the permanent magnet material. The hole 83 in the main permanent magnet 61 may be represented as a superposition of two permanent magnet cylinders of the same magnet material being magnetized to the same value of $B_r$ but having opposite magnetization directions. Since each of the superimposed magnets in this representation produces the same magnetic field strength, equal to $B_r/2$, but in opposite directions, there exists substantially zero magnetic field strength inside the hole 83. Furthermore, when the permanent magnet cylinder 62 and the hole 83 are coaxial with each other, the magnetic field direction outside the permanent magnet 62, having the hole 83 as shown in FIG. 2 is the same as for a solid cylindrical permanent magnet. Only the field strength is reduced in proportion to reduction of the cross sectional area of the magnet assembly 61 by including the hole 83.

To keep the length of the magnet 61 as short as is practical, it is preferable to compensate end effects by using the end magnets 63, 64 as shown in FIG. 2 and previously described herein. FIG. 8 shows a graphic representation of the effect of the end magnets (63, 64 in FIG. 2) on the magnetic field inside the magnet hole (83 in FIG. 2) as well as outside the magnet (62 in FIG. 2) at a 12 inch diameter sensitive volume (58 in FIG. 2). The graph of FIG. 8 represents the magnetic field generated by the magnet assembly 61 which is especially suitable for use in slim bore holes. The permanent magnet 62 for use in slim wellbores can have a 6.6 cm diameter and 100 cm length. The permanent magnet 62 can be formed from ferrite permanent magnet material such as sold under trade name "Spinalor" and manufactured by Ugimag, 405 Elm St., Valparaiso, Ind., or sold under trade name "Permadure" and manufactured by Philips, 230 Duffy Ave., Nicksville, N.Y. The magnet material described herein has 0.42 T remanence induction. The top end magnet 63 and the bottom end magnet 64 can also be 6.6 cm diameter cylinders about 18.5 cm in length and placed at a distance of 3.5 cm from the ends of the main magnet 62. The end magnets 63, 64 can be made from a permanent magnet material such as neodymium-iron-boron material sold under trade name "Ugistab" and manufactured by Ugimag, 405 Elm St., Valparaiso, Ind. or sold under trade name "Vacodym" and manufactured by Vacuumschmeize GMBH, 9/7 Rhenaniastrasse St., Berlin, Germany. The neodymium-iron-boron material typically has a remanence induction of about 1T.

3. Magnetoacoustic and Magnetostrictive Ringing

As is understood by those skilled in the art, determination of properties of interest of the earth formations (such as 26 in FIG. 1) require that an NMR well logging instrument be able to measure short duration values of a magnetic resonance parameter referred to as T2. Some nuclear magnetic resonance phenomena decay in amplitude very quickly, as is understood by those skilled in the art. In order to measure these short duration events, the NMR well logging apparatus should have as short "dead time" as ia practical. Dead time of an NMR logging system is affected by, among other things, magnetoacoustic interaction which may produce an unwanted signal in the transceiver antenna (such as 67 in FIG. 2). This section of the description of the preferred embodiment will explain how the NMR logging apparatus of the present invention reduces the effects of magnetoacoustic interaction to reduce the dead time.

Different types of magnetoacoustic interaction may produce a parasitic signal in the NMR antenna. Antenna wiring and other metal parts of the NMR probe (42 in FIG. 2) can be affected by the permanent magnet's (62 in FIG. 2) magnetic field and the RF field generated by passing RF pulses through the transceiver antenna 67. These fields can produce spurious "ringing" which is well known to those skilled in the art as "coil disease". This type of ringing is excited by the Lorenz force. As explained in E. Fukushima et. al., *Spurious Ringing in Pulse NMR,* J. Magn. Res. v. 33, pp. 199–203, 1979, the efficiency of conversion of RF radiation into acoustical waves, and vice versa, is directly proportional to square of the static magnetic field intensity at the location of the antenna.

In the present invention, the RF transmitting antenna (referred to as the transceiver antenna and shown at 67 in FIG. 2) is positioned in the magnet hole (83 in FIG. 2), wherein there is substantially zero static magnetic field from the permanent magnet 62. This type of magnetoacoustic ringing is substantially eliminated by the transceiver antenna 67 configuration of the present invention.

Another source of magnetoacoustic interaction is magnetostrictive ringing. Magnetostrictive ringing is typically caused when non-conductive magnetic material, such as magnetic ferrite are used in the antenna. The magnetoelastic interaction in the magnetically soft ferrite rod (68 in FIG. 2) used in the transceiver antenna 67 and the hard ferrite used in the permanent magnet 62 are different from each other.

Magnetostrictive ringing of the magnetically soft ferrite rod (68 in FIG. 2) in the antenna 67 is removed if cessation of the RF power pulse leaves the ferrite 68 completely demagnetized. This magnetization condition is met within the magnet hole 83.

Figure 9:
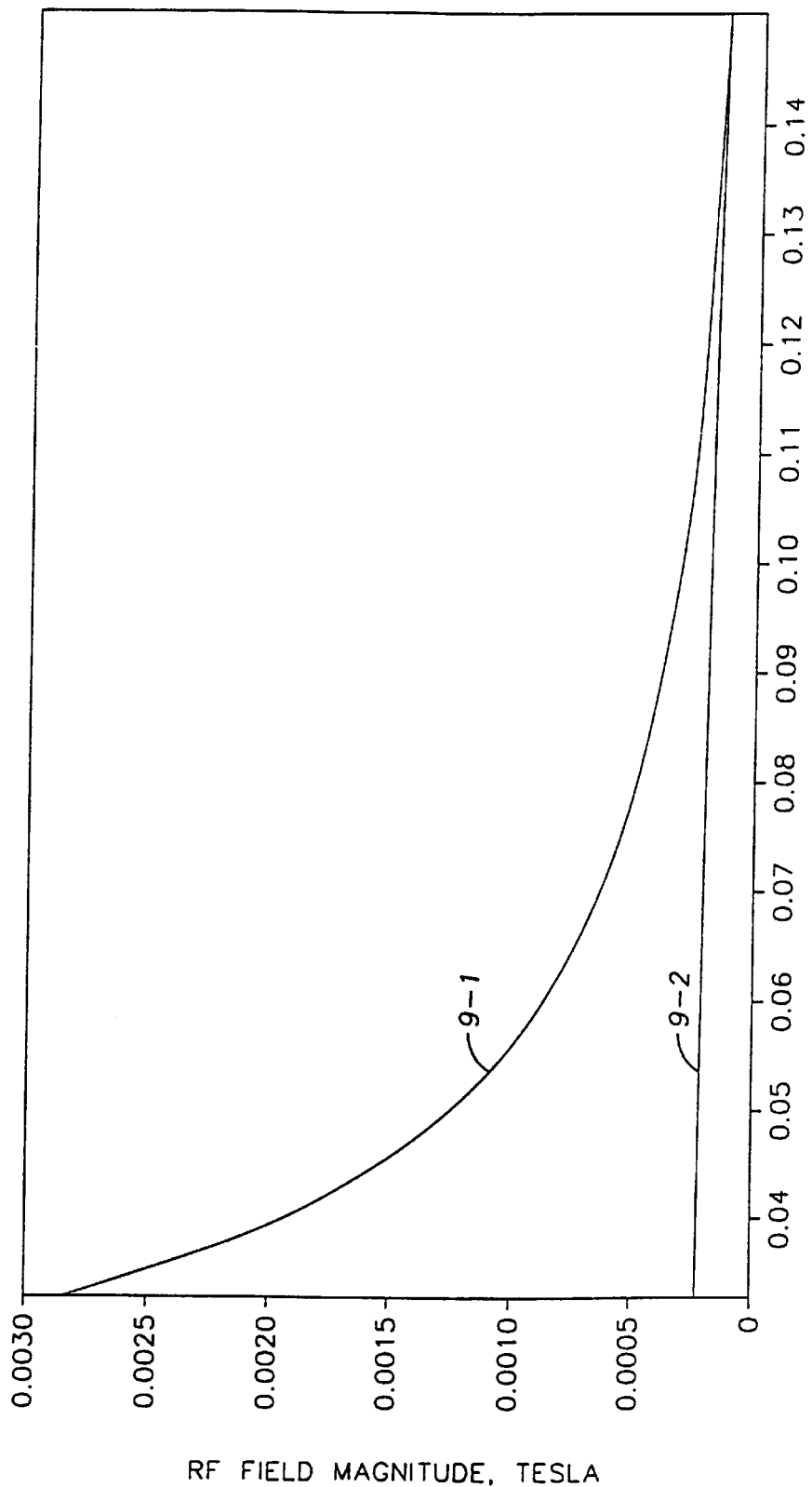
FIG. 9 shows a graph of radial dependence of RF field strength for transversal and longitudinal dipole antennas.

A spurious signal generated by the permanent magnet 62, which continues to vibrate upon cessation of the RF pulse is a direct consequence of the inverse effect of magnetostriction. Two features of the present invention substantially reduce ringing of the magnet 62. First, the radial dependence of the RF field strength, as previously explained herein, is relatively small when compared with that of prior art NMR logging instruments. The relatively small radial dependence is a result of the use of the longitudinal dipole antenna with the ferrite rod (67 and 68 in FIG. 2). Second is the use of an orthogonal receiver coil. In the present invention, the additional receiver coil (70 in FIG. 2) is substantially orthogonal to the transceiver coil 67 and so meets this requirement. FIG. 9 shows a graph of the radial dependence of the RF field strength for the longitudinal (transceiver antenna 67), at curve 9-1, and for the transversal dipole (additional receiver coil 70) antenna at curve 9-2, from which it is apparent that the RF field affecting the permanent magnet 62 does not significantly exceed $B_1$ at radius $R=R_{sv}$. That magnitude of RF magnetic field is typically not sufficient to effectively excite acoustic waves. The orthogonal receiver antenna (additional receiver coil 70) in the preferred embodiment of the invention substantially removes coupling of the additional receiver coil (70 in FIG. 2) with parasitic magnetic flux due to the inverse effect of magnetostriction.

Thus, the total magnetoacoustic ringing in the NMR probe (42 in FIG. 1) of the present invention is reduced significantly compared with NMR logging instruments of the prior art.

4. Considerations for Making Measurements While Moving the NMR Probe Within the Wellbore FIG. 3 shows a sectional view of the apparatus of FIG. 1 taken in a plane parallel to the axis of the permanent magnet 62 (indicated by lines II—II in FIG. 1). The sectional view in FIG. 3 more clearly illustrates the relative dimensions of the permanent magnet 62, the transceiver antenna 67 and the additional receiver antenna 70. In well logging practice there are two particularly common sets of wellbore conditions which should be accounted for in building the NMR logging apparatus according to the present invention. In the first set of conditions the nominal diameter of the wellbore (22 in FIG. 1) is within a range of 7 inches to 12 inches. The external diameter of the NMR probe 42 for use in this range of wellbore diameters can be about 6 inches.

The present invention has the capability of selectively varying the RF frequency which enables illustration of a particular advantage of the present invention. The advantage will be illustrated by the following example: assume the wellbore 22 diameter to be 8 inches and the sensitive volume (58 in FIG. 1) diameter selected to be 20 inches and 36 inches. The permanent magnet 62 axial length can be about 40 inches. This axial length for the permanent magnet 62 can provide about 30 inch axial length having substantially equal axial strength static magnetic field in the earth formation (26 in FIG. 1). The static magnetic field strength decreases monotonically with increasing radial distance from the longitudinal axis 78. In the preferred embodiment of the invention the hydrogen nuclei in the sensitive volume 58 are prepolarized by the static magnetic field almost at equilibrium. The transceiver antenna 67 has axial length of about 24 inches and generates an adequate strength RF magnetic field for NMR experiments along a 24 inch long cylindrical volume. The transceiver antenna 67 can be positioned in the magnet hole 83 so that the cylindrical volume of the RF field can be positioned near the lowermost part of the static magnetic field's cylindrical volume. The receiving antenna can be about 18 inches long and is positioned to receive the NMR signal mainly from a cylindrical volume which can be located near the lowermost part of the static magnetic field volume. The present embodiment of the invention provides a static magnetic field long enough so that the NMR probe 42 may move a significant axial distance while still applying an RF magnetic field which is disposed entirely within the region of the earth formation which is prepolarized by the static magnetic field. The receiver antenna aperture of the present invention is such that the NMR probe 42 may move a significant axial distance while enabling the receiver antenna to receive NMR signals only from those volumes which have been completely energized by the RF field. The present invention is therefore capable of performing a proper steady state Carr-Purcell-Meiboom-Gill (CPMG) measurement sequence run entirely within in a cylindrical volume 18 inches long. It is to be understood that the relative axial positions of the permanent magnet 62, transceiver antenna 67 and additional receiver antenna 70 are intended only as an example for a probe intended for use in more common well logging applications in which the measurements are made while the probe is withdrawn from the wellbore (22 in FIG. 1). It is to be understood that the axial length and positions of the magnet 62 and antennas 67, 70 could as easily be adapted for logging while the instrument is lowered into the wellbore 22 by reversing the relative axial positions of the magnet 62 and antennas 67, 70.

Figure 11:
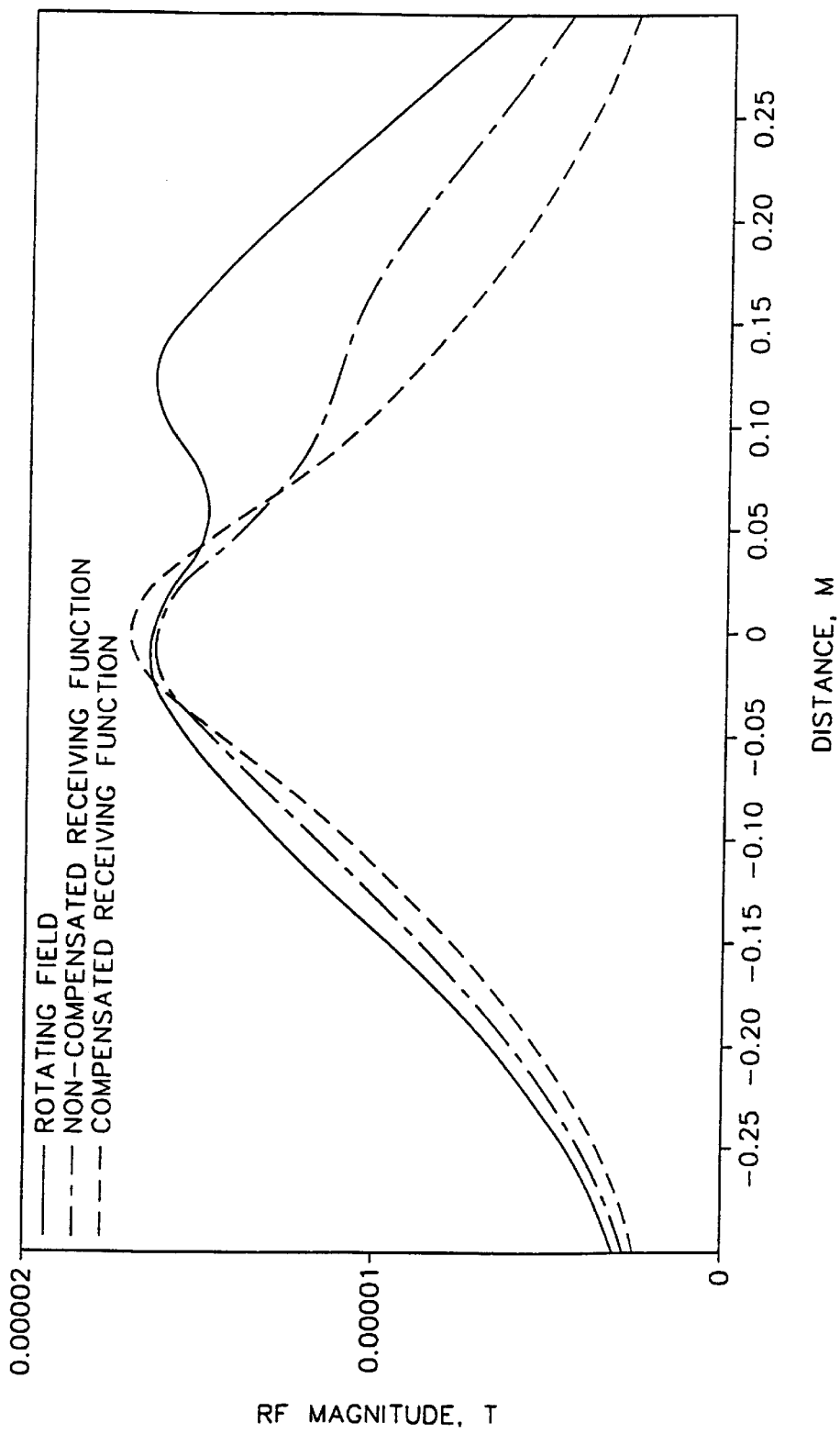
FIG. 11 shows spatial distribution of the effective RF magnetic field for the antenna shown in FIG. 10.

The second set of conditions includes wellbores having nominal diameters between about 4 inches and 7 inches. The NMR probe 42 external diameter in this example can be about 3⅝ inches. The present example includes a wellbore 22 having a diameter of about 5 inches, and sensitive volume 58 diameters of about 7 inches and 12 inches. The permanent magnet 62 axial length in this example can be about 80 cm. This axial length for the permanent magnet 62 provides about 45 cm length of axially equal magnetic field strength. Referring now to FIG. 10, an arrangement of a high vertical resolution RF antenna is presented. The main part 168A of the transceiver antenna 67 can be about 15 cm length and 1 cm diameter. The prepolarizing part 69 of the antenna 67 can be about 7.5 cm length and 1 cm diameter and is typically placed at a distance about 1 cm from the main part 168A. A compensating receiver coil 71 serves to compensate of the magnetizing effect of the main part 168A on the prepolarizing part 69. FIG. 11 shows a graph of the spatial distribution of the effective RF field (orthogonal to static magnetic field component of RF field) and the antenna receiving sensitivity function which is presented in the form of the RF field distribution. The effect of compensating the receiver coil 66 is also illustrated.

DESCRIPTION OF AN ALTERNATIVE EMBODIMENT

As is understood by those skilled in the art, the wellbore (22 in FIG. 1) can sometimes have a large enough diameter, due to "washouts" or similar effects known in the art to cause the sensitive volume (58 in FIG. 1) of the first embodiment of the invention to be positioned within the wellbore 22 itself rather than wholly within the earth formation (such as 26 in FIG. 1). An alternative embodiment of the present invention particularly suited for use in such situations can be better understood by referring to FIG. 12. The permanent magnet 62A, which in the first embodiment of the invention (62 in FIG. 2) includes a magnet hole (83 in FIG. 2), in the present embodiment includes a magnet hole 83A which is radially displaced towards the outer surface of the magnet 62A. A transceiver antenna 67A, which can be substantially the same in design as the transceiver antenna (67 in FIG. 2) of the first embodiment, can include coil windings 66A in planes substantially perpendicular to the longitudinal axis 78, a ferrite rod 68A inside the coil windings 66A, and optionally a frequency control coil 101A wound on the ferrite rod 68A. The transceiver antenna 67A can be disposed generally in the center of the magnet hole 83A. An additional receiver antenna 70A can be disposed on the outer surface of the magnet 62A as shown in FIG. 12 and is generally centered about an axis 103 which intersects the longitudinal axis 78 and the center of the magnet hole 83A. The axis 103 is typically perpendicular to the magnetization direction 105 of the magnet 62A.

FIG. 13 shows a cross-sectional view of the arrangement shown in FIG. 12 to better explain the relative placement of the components of the present embodiment of the invention. The magnet 62A is shown generally eccentered in the wellbore 22A so as to be impressed against the wall of the wellbore 22A. The sensitive volume 58A is typically selected, by appropriate selection of RF frequency for the power pulses conducted through the transceiver antenna 67A, to be at a depth into the earth formation 26A of about 5 cm from the wellbore wall. Geometrical considerations in selection of appropriate frequency include first that the sensitive volume radius ($R_{sv}$) should exceed the quantity $2R_{bh}-R_m$ wherein $R_{bh}$ represents the wellbore radius and $R_m$ represents the radius of the magnet 62A. Second, the effective diameter $d_a$ of the additional receiver antenna 70A can be approximately equal to the quantity $2R_{sv}-R_m$. Axial length considerations for the magnet 62A, the transceiver antenna 67A and the additional receiver antenna 70A can be substantially the same as in the first embodiment of the invention.

Figure 14:
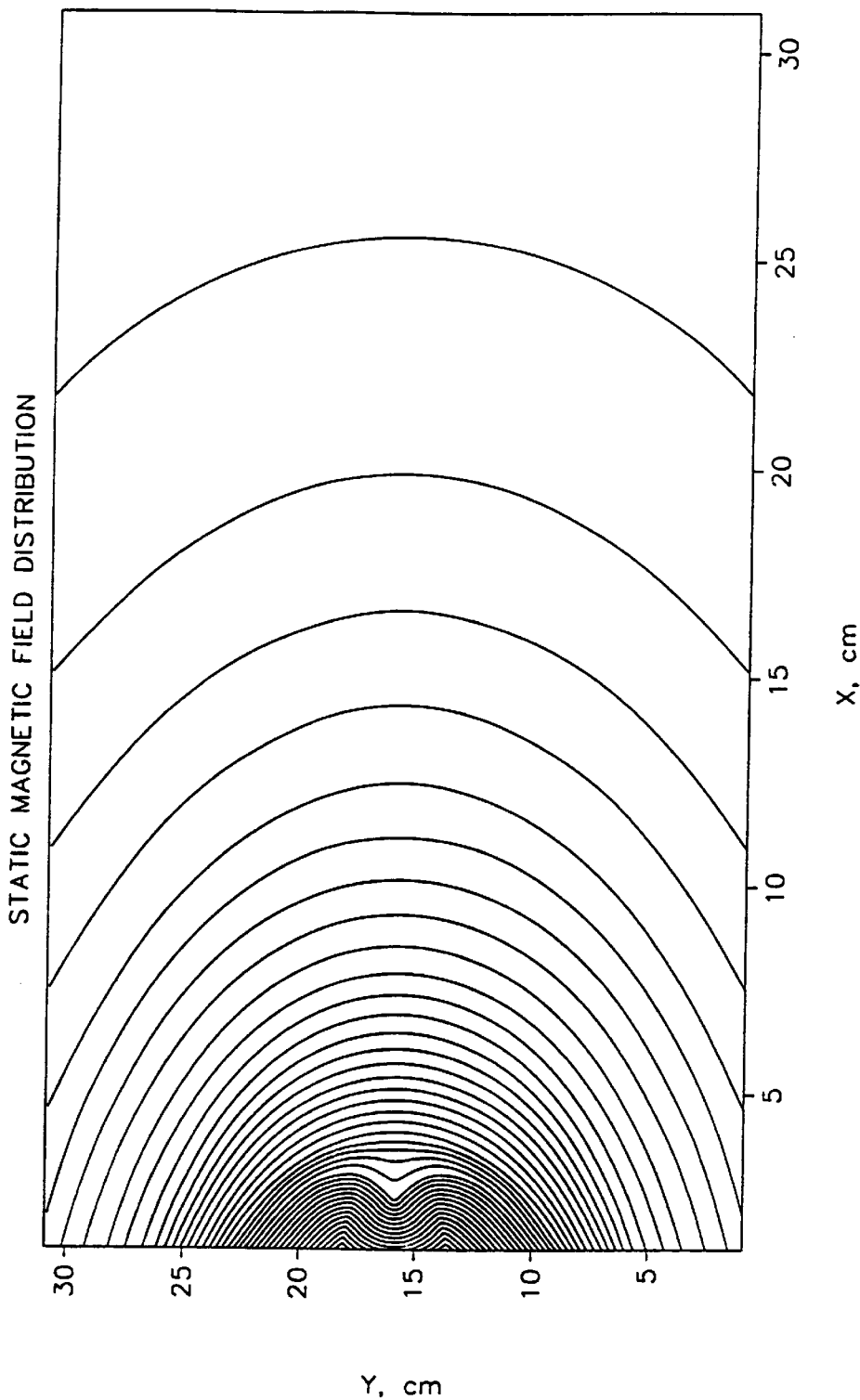
FIG. 14 shows a graph of the static magnetic field strength for the magnet in the arrangement in FIGS. 12 and 13.

FIG. 14 shows the a graph of the strength of the static magnetic field generated by the magnet 62A of the present embodiment. As can be observed in FIG. 14, asymmetry in the static field near the surface of the magnet 62A is largely absent at the radial depth selected for the sensitive volume 58A.

Figure 15:
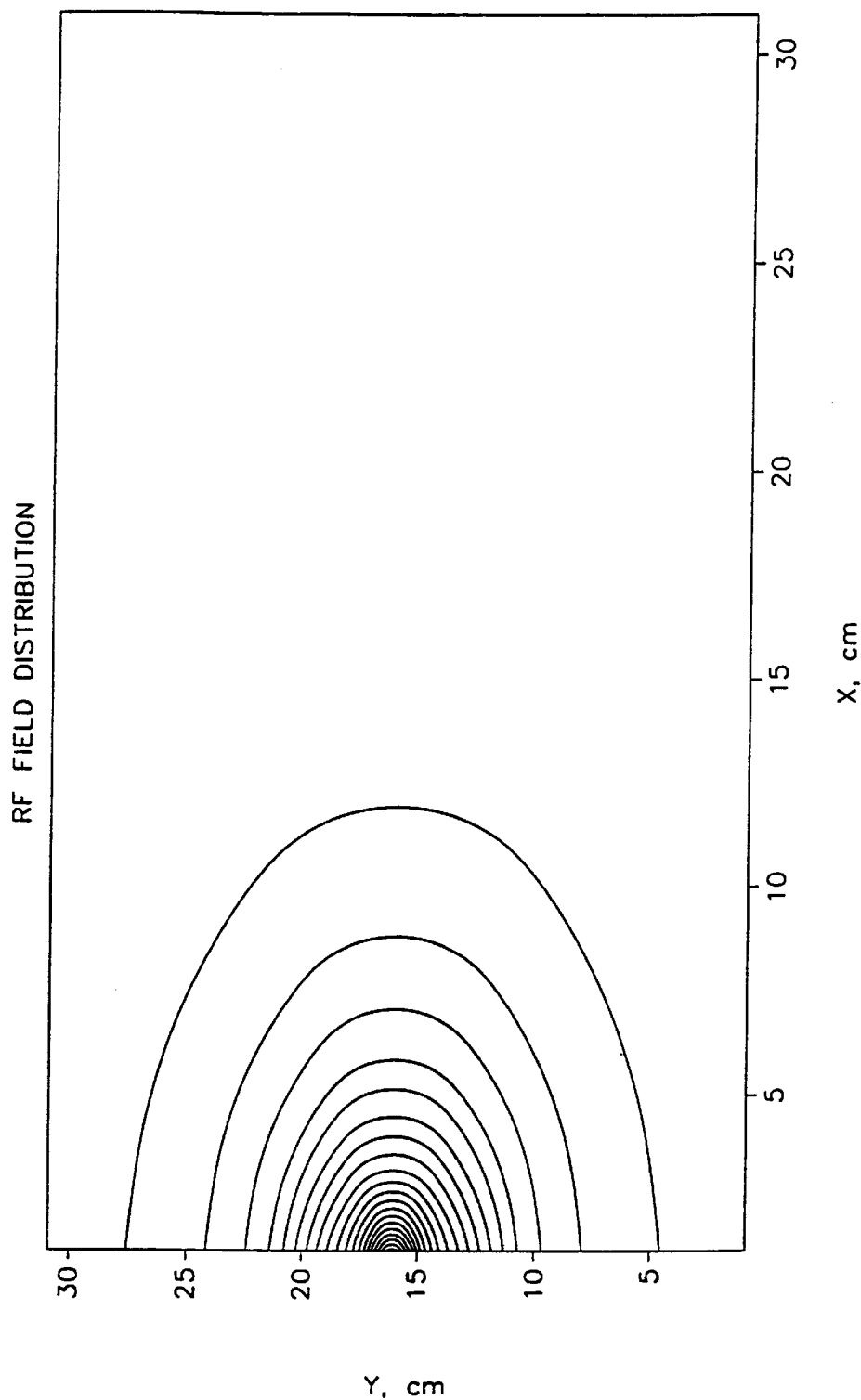
FIG. 15 shows the a graph of RF field strength for the transceiver antenna in the arrangement of FIGS. 12 and 13.

FIG. 15 shows an X-Y coordinate contour graph of the radial distribution of magnitude of the RF magnetic field generated by the transceiver antenna 67A. As can be observed in FIG. 15, the RF field is substantially symmetric about the axis (103 in FIG. 13).

Figure 16:
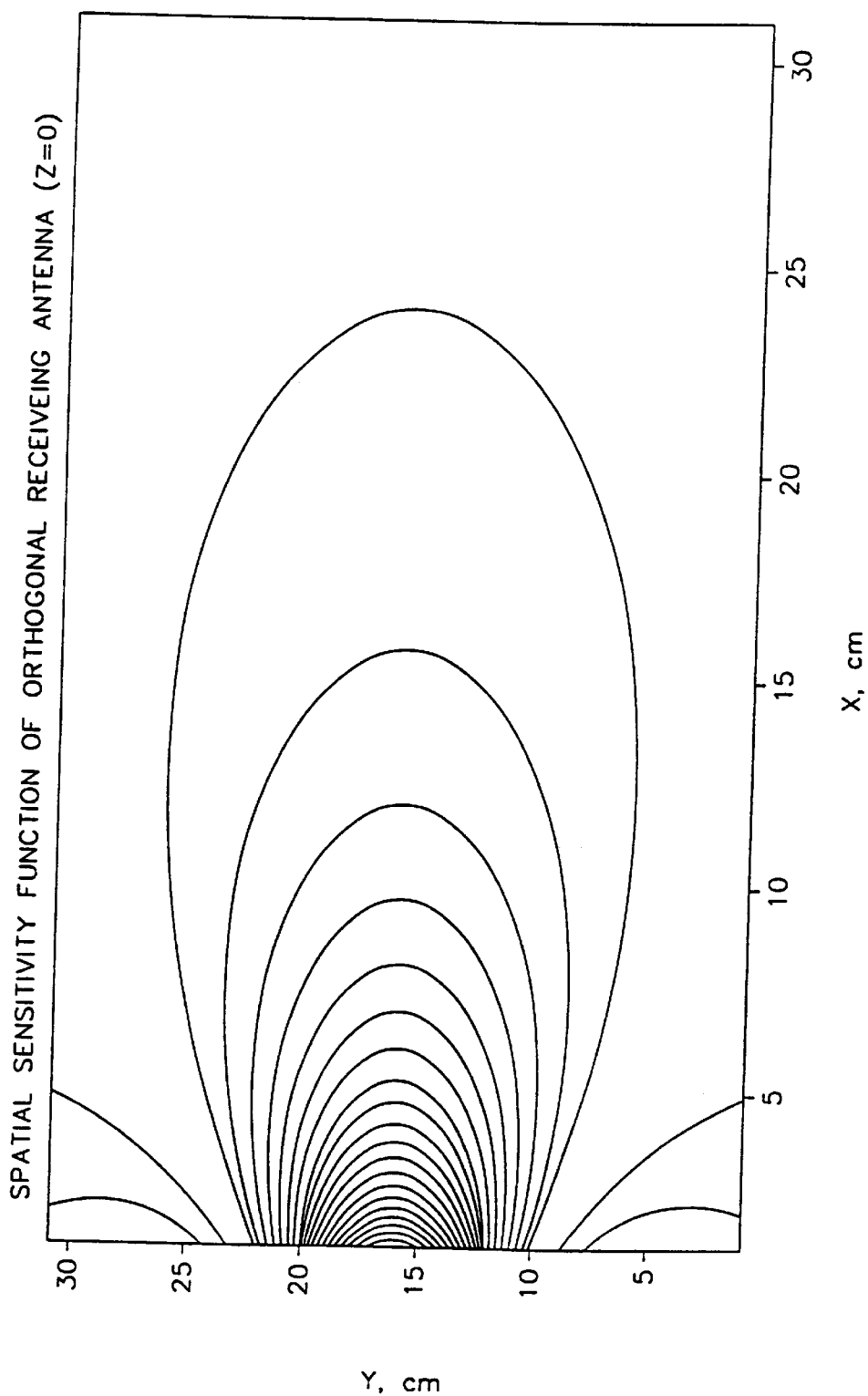
FIG. 16 shows a graph of the spatial sensitivity of the additional receiver antenna for the arrangement of FIGS. 12 and 13.

FIG. 16 shows an X-Y coordinate contour graph of the sensitivity of the additional receiver antenna (70A in FIG. 12). The sensitivity of the additional receiver antenna 70A is substantially symmetric about the axis 103.

Figure 17:
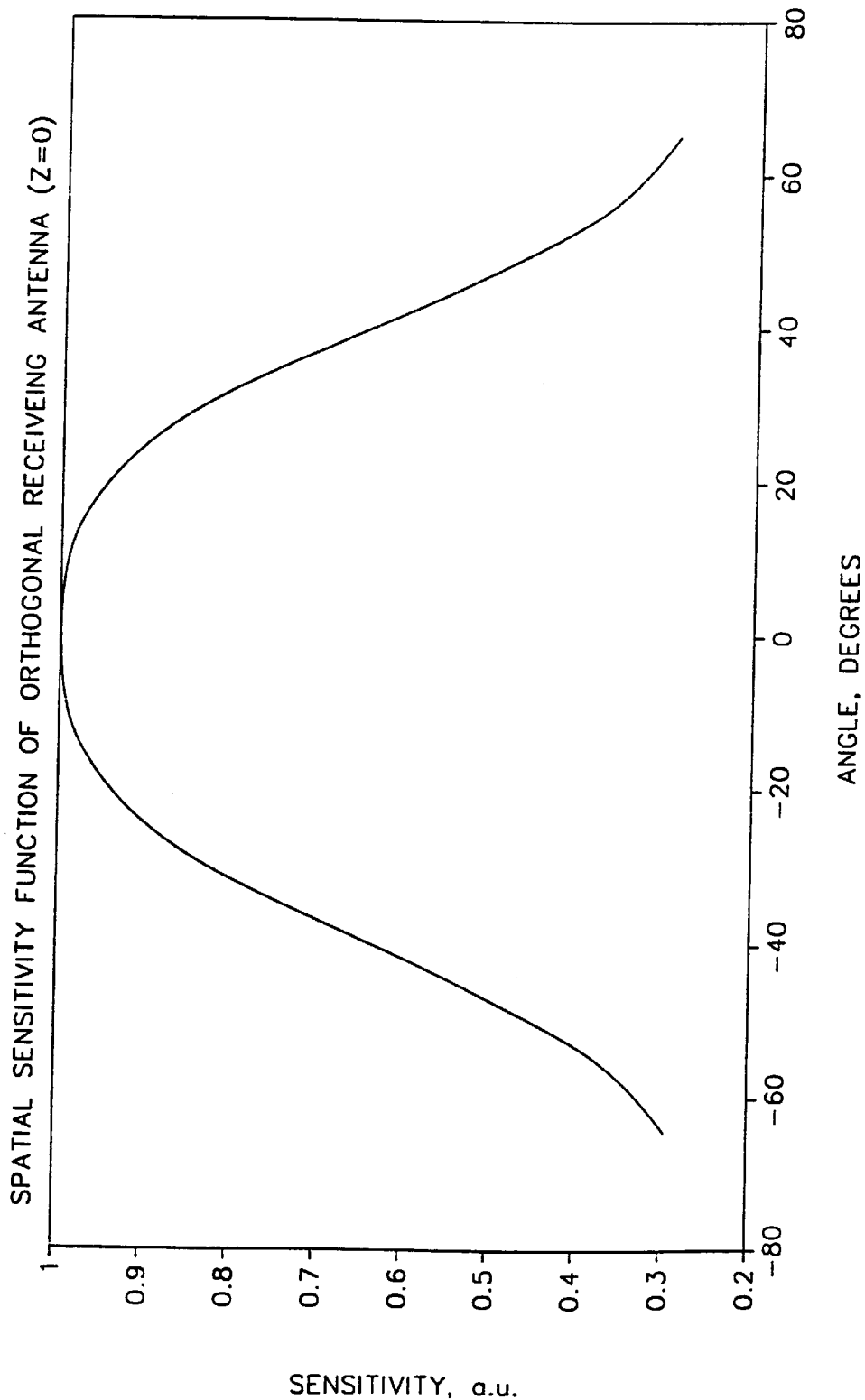
FIG. 17 shows a graph of the angular distribution of sensitivity for the additional receiver antenna in the arrangement of FIGS. 12 and 13.

FIG. 17 shows a graph of the radial sensitivity function for the additional receiver antenna 70A (which was plotted in FIG. 16 in X-Y coordinate contour form) as a function of angular deviation from the axis 103. The graph of FIG. 17 shows that the sensitivity of the additional receiver antenna 70A is substantially confined to a "window" subtending an angle of about 120 degrees.

It will be readily appreciated by persons skilled in the art that the present invention is not limited to what has been particularly shown and described herein. Rather the scope of the present invention should be limited only by the claims which follow.

What is claimed is:

1. A nuclear magnetic resonance sensing apparatus, comprising:
    a magnet for inducing a static magnetic field within a first region containing materials to be analyzed, said magnet inducing substantially zero static magnetic field within a second region proximal to said magnet;
    means for generating a radio frequency magnetic field in said first region for exciting nuclei of said materials to be analyzed, said means for generating comprising an antenna disposed within said second region; and
    means for receiving a nuclear magnetic resonance signal from said excited nuclei.

2. The apparatus as defined in claim 1 wherein said antenna comprises a wire coil.

3. The apparatus as defined in claim 2 further comprising a high magnetic permeability ferrite disposed proximal to said wire coil.

4. The apparatus as defined in claim 3 further comprising a frequency control coil disposed proximal to said high magnetic permeability ferrite for selectively varying a static magnetic field level at said high magnetic permeability ferrite, said frequency control coil providing selective variation of the magnetic permeability of said high magnetic permeability ferrite thereby selectively controlling a tuning frequency of said antenna.

5. The apparatus as defined in claim 4 wherein said wire coil comprises a prepolarizing part and a main part, said main part being longer along an axis of said apparatus than said prepolarizing part.

6. The apparatus as defined in claim 5 wherein said prepolarizing part comprises a compensating coil for reducing magnetization of said prepolarizing part by said main part.

7. A method for nuclear magnetic resonance sensing comprising:
    inducing a static magnetic field of substantially equal amplitude within a first region containing materials to be analyzed, said static magnetic field comprising a second region having substantially zero static magnetic field;
    generating a radio frequency magnetic field within said first region for exciting nuclei of said materials, said step of generating performed from within said second region; and
    receiving nuclear magnetic resonance signals from said excited nuclei.

8. The method as defined in claim 7 wherein said step of receiving said nuclear magnetic resonance signal is performed from within said second region having substantially zero static magnetic field.

9. The method as defined in claim 8 wherein said step of generating is performed by an antenna including a high magnetic permeability ferrite disposed proximal to said antenna.

10. The method as defined in claim 9 further comprising selectively varying a static magnetic field level in said high magnetic permeability ferrite, thereby selectively varying magnetic permeability of said high magnetic permeability ferrite so that a tuning frequency of said antenna is selectively varied and a frequency of said radio frequency magnetic field is selectively varied.

11. The method as defined in claim 7 wherein said step of generating is performed by a first antenna which is substantially orthogonal to a second antenna used to perform said step of receiving.

12. The method as defined in claim 11 further comprising the step of adjusting responses of said first and of said second antennas to have substantially zero mutual inductance.

* * * * *